(12) United States Patent
Dragic et al.

(10) Patent No.: US 6,908,734 B2
(45) Date of Patent: Jun. 21, 2005

(54) SULFATED CCR5 PEPTIDES FOR HIV-1 INFECTION

(75) Inventors: Tatjana Dragic, Scarsdale, NY (US); William C. Olson, Ossining, NY (US)

(73) Assignees: Progenics Pharmaceuticals, Inc., Tarrytown, NY (US); Aaron Diamond AIDS Research Centre, New York, NY (US)

( * ) Notice: Subject to any disclaimer, the term of this patent is extended or adjusted under 35 U.S.C. 154(b) by 35 days.

(21) Appl. No.: 10/323,314

(22) Filed: Dec. 19, 2002

(65) Prior Publication Data

US 2003/0139571 A1 Jul. 24, 2003

Related U.S. Application Data

(63) Continuation of application No. 09/796,202, filed on Feb. 28, 2001, now Pat. No. 6,548,636.
(60) Provisional application No. 60/267,231, filed on Feb. 7, 2001, provisional application No. 60/205,839, filed on May 19, 2000, and provisional application No. 60/185,667, filed on Feb. 29, 2000.

(51) Int. Cl.[7] .......................... C12Q 1/70; C12P 21/06; C12N 5/00; C07K 16/00; A61K 39/21
(52) U.S. Cl. .......................... 435/5; 435/69.1; 435/325; 435/339.1; 530/388.35; 424/208.1
(58) Field of Search .......................... 435/5, 69.1, 325; 435/339.1; 530/358.35; 424/208.1

(56) References Cited

PUBLICATIONS

Baba, et al., (1998) "Mechanism of Inhibitory Effect of Dextran Sulfate and Heparin on Replication of Human Immunodeficiency Virus In Vitro", *Proc. Natl. Acad. Sci. U.S.A.* 85:6132–6135.

Baulerle and Huttner, (1987) "Tyrosine Sulfation Is a trans-Golgi-specific Protein Modification", *Cell Biol.* 105:2655–2663.

Blanpain, C., et al. (1999) "Multiple Charged and Aromatic Residues in CCR5 Amino-terminal Domain Are Involved in High Affinity Binding of Both Chemokines and HIV–1 Env Protein", *J. Biol. Chem.* 274:34719–34727.

Cormier, E.G., et al., (2000) "Specific Interaction of CCR5 Amino-terminal Domain Peptides Containing Sulfotyrosines With HIV–1 Envelope Glycoprotein gp120" *Proc. Nat. Acad. Sci. U.S.A.* 97:5762–5767.

(Continued)

*Primary Examiner*—Hankyel T. Park
(74) *Attorney, Agent, or Firm*—John P. White; Cooper & Dunham LLP

(57) ABSTRACT

This invention provides a compound comprising the structure: θαYDINYYTSEβλ wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein λ represents a carboxyl group or an amidated carboxyl group; wherein all of α,Y,D,I,N,Y,Y,T,S,E and β are joined together by peptide bonds; further provided that at least two tyrosines in the compound are sulfated.

12 Claims, 13 Drawing Sheets

PUBLICATIONS

Doranz, B. J. et al. (1997) "Two Distinct CCR5 Domains Can Mediate Coreceptor Usage By Human Immunodeficiency Virus Type 1", *J. Virol.* 71:6305–6314.

Dragic, T. et al., (1998) "Amino–terminal Substitutions in The CCR5 Coreceptor Impair gp120 Binding and Human Immunodeficiency Virus Type 1 Entry", *J. Virol.* 72:279–285.

Farzan, M., et al., (1998) "A Tyrosine–Rich Region in the N Terminus of CCR5 Is Important for Human Immunodeficiency Virus Type 1 Entry and Mediates an Association Between gp120 and CCR5", *J. Virol.* 72:1160–1164.

Farzan M., et al. (2000) "A Tyrosine–sulfated Peptide Based on the N Terminus of CCR5 Interacts with a CD4–enhanced Epitope of the HIV–1 gp120 Envelope Glycoprotein and Inhibits HIV–1 Entry", *J. Biol. Chem.* 275:33516–33521.

Farzan, M., et al. (1999) "Tyrosine Sulfation of the Amino Terminus of CCR5 Facilitates HIV–1 Entry", *Cell* 96:667–676.

Hwang, S. S., et al., (1991) "Identification of the Envelope V3 Loop as the Primary Determinant of Cell Tropism in HIV–1" *Science* 253:71–74.

Rabut, G. E., et al., (1998) "Alanine Substitutions of Polar and Nonpolar Residues in the Amino–Terminal Domain of CCR5 Differently Impair Entry of Macrophage–and Dual-tropic Isolates of Human Immunodeficiency Virus Type 1", *J. Virol.* 72:3464–3468.

Rodriguez, G., et al., (1995) "Mediation of Human Immunodeficiency Virus Type 1 Binding by Interaction of Cell Surface Heparan Sulfate Proteoglycans with the V3 Region of Envelope gp120–gp41", *J. Virol.* 69:2233–2239.

FIGURE 1
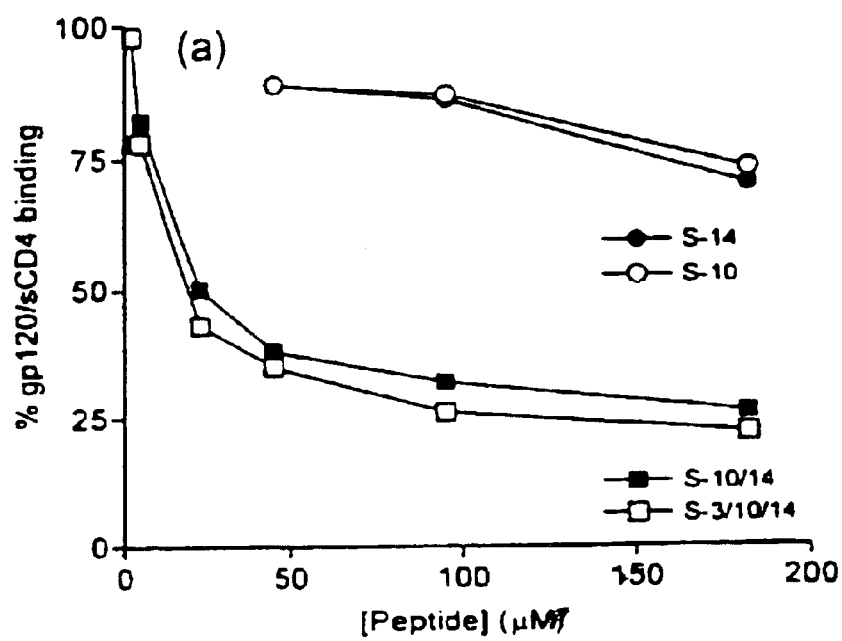
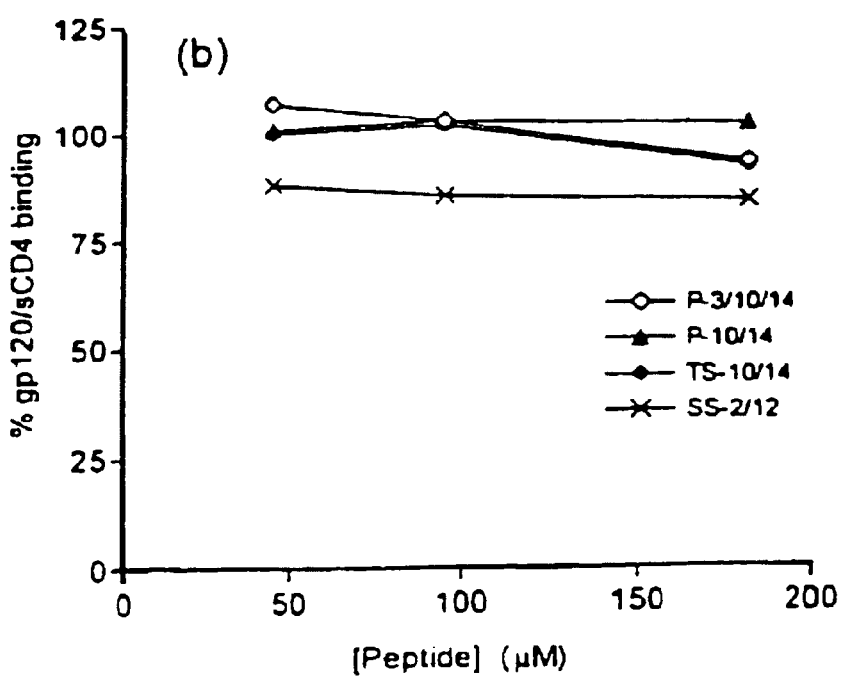

FIGURE 6

| SEQUENCE | LABEL |
|---|---|
| Unmodified peptide | |
| D Y Q V S S P I Y D I N Y Y T S E | 3/10/14 |
| Sulfated peptides | |
| D Y Q V S S P I Y D I N Y Y T S E | S-3/10/14 |
| D Y Q V S S P I Y D I N Y Y T S E | S-10/14 |
| D Y Q V S S P I Y D I N Y Y T S E G A G K-biotin | bS-10/14 |
| D Y Q V S S P I Y D I N Y Y T S E | S-10 |
| D Y Q V S S P I Y D I N Y Y T S E | S-14 |
| D Y Q V S S P I Y D I N Y Y | TS-10/14 |
| Phosphorylated peptides | |
| D Y Q V S S P I Y D I N Y T S E | P-3/10/14 |
| D Y Q V S S P I Y D I N Y Y T S E | P-10/14 |
| D Y Q V S S P I Y D I N Y T S E G A G K-biotin | bP-10/14 |
| Sulfated and Scrambled peptides | |
| Y V S Q P D N T Y I Y S Y E S I D | SS-2/12 |
| S I D I Y N P T Y V S N Y E S D Y | SS-10/14 |

FIGURE 12

| Amino acid sequence | Name |
|---|---|
| Sulfated peptides | |
| D Y Q V S S P I Y D I N Y Y T S E | 2-18 |
|         P I Y D I N Y Y T S E | 10-18 |
|         P I Y A I N Y Y T S A | 10-18(11A/18A) |
|       S P I Y D I N Y – – – – | 8-15 |
|             D I N Y Y T – – | 6-16 |
|         P I Y D I N Y – – – – | 10-15 |
| Phosphorylated peptides | |
| D Y Q V S S P I [Y] D I N [Y] Y T S E | 2-18(P) |

FIGURE 13

| | | |
|---|---|---|
| C5 | R 469 | 100 |
| C4 | R 444 | 44 |
| | Q 442 | 40 |
| | R 440 | 32 |
| | K 432 | 40 |
| | Q 428 | 100 |
| | W 427 | 100 |
| | N 425 | 96 |
| | Q 422 | 100 |
| | K 421 | 100 |
| | I 420 | 100 |
| | R 419 | 63 |
| C3 | P 369 | 48 |
| | H 363 | 24 |
| V3 | R 326 | 100 |
| | I 325 | 100 |
| | D 324 | 88 |
| | I 322 | 92 |
| | E 320 | 38 |
| | T 318 | 100 |
| | Y 316 | 100 |
| | F 315 | 84 |
| | R 313 | 54 |
| | G 312 | 100 |
| | P 311 | 96 |
| | G 310 | 100 |
| | S 306 | 88 |
| | T 303 | 100 |
| | N 301 | 96 |
| | R 298 | 100 |
| C2 | K 282 | 96 |
| | N 280 | 100 |
| | N 279 | 56 |
| C1 | T 123 | 100 |
| | K 121 | 96 |

SEQUENCE LISTING

```
<160> NUMBER OF SEQ ID NOS: 17

<210> SEQ ID NO 1
<211> LENGTH: 352
<212> TYPE: PRT
<213> ORGANISM: human

<400> SEQUENCE: 1

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45
```

```
Met Leu Val Ile Leu Ile Leu Ile Asn Cys Lys Arg Leu Lys Ser Met
         50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Gln Trp Asp Phe
                 85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
                260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
        290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 2
<211> LENGTH: 1376
<212> TYPE: DNA
<213> ORGANISM: human

<400> SEQUENCE: 2
gaattccccc aacagagcca agctctccat ctagtggaca gggaagctag cagcaaacct      60
tcccttcact acaaaacttc attgcttggc caaaaagaga gttaattcaa tgtagacatc     120
tatgtaggca attaaaaacc tattgatgta taaaacagtt tgcattcatg gagggcaact     180
aaatacattc taggacttta taaaagatca cttttatttt atgcacaggg tggaacaaga     240
tggattatca agtgtcaagt ccaatctatg acatcaatta ttatacatcg gagccctgcc     300
aaaaaatcaa tgtgaagcaa atcgcagccc gcctcctgcc tccgctctac tcactggtgt     360
tcatctttgg ttttgtgggc aacatgctgg tcatcctcat cctgataaac tgcaaaaggc     420
```

```
tgaagagcat gactgacatc tacctgctca acctggccat ctctgacctg ttttccttc      480 ttactgtccc cttctgggct cactatgctg ccgcccagtg ggactttgga aatacaatgt      540
gtcaactctt gacagggctc tattttatag gcttcttctc tggaatcttc ttcatcatcc      600
tcctgacaat cgataggtac ctggctgtcg tccatgctgt gtttgcttta aaagccagga      660
cggtcacctt tggggtggtg acaagtgtga tcacttgggt ggtggctgtg tttgcgtctc      720
tcccaggaat catctttacc agatctcaaa agaaggtct tcattacacc tgcagctctc       780
attttccata cagtcagtat caattctgga gaatttcca gacattaaag atagtcatct       840
tggggctggt cctgccgctg cttgtcatgg tcatctgcta ctcgggaatc ctaaaaactc      900
tgcttcggtg tcgaaatgag aagaagaggc acagggctgt gaggcttatc ttcaccatca      960
tgattgttta ttttctcttc tgggctccct acaacattgt ccttctcctg aacaccttcc     1020
aggaattctt tggcctgaat aattgcagta gctctaacag gttggaccaa gctatgcagg     1080
tgacagagac tcttgggatg acgcactgct gcatcaaccc catcatctat gcctttgtcg     1140
gggagaagtt cagaaactac ctcttagtct tcttccaaaa gcacattgcc aaacgcttct     1200
gcaaatgctg ttctattttc cagcaagagg ctcccgagcg agcaagctca gtttacaccc     1260
gatccactgg ggagcaggaa atatctgtgg cttgtgaca cggactcaag tgggctggtg     1320
acccagtcag agttgtgcac atggcttagt tttcatacac agcctgggct gggggt         1376

<210> SEQ ID NO 3
<211> LENGTH: 49
<212> TYPE: PRT
<213> ORGANISM: human immunodeficiency virus

<400> SEQUENCE: 3

Arg Gln Leu Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Val Glu Arg Tyr Leu Lys Asp
        35                  40                  45

Gln

<210> SEQ ID NO 4
<211> LENGTH: 35
<212> TYPE: PRT
<213> ORGANISM: human immunodeficiency virus

<400> SEQUENCE: 4

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu
        35

<210> SEQ ID NO 5
<211> LENGTH: 22
<212> TYPE: PRT
<213> ORGANISM: human
```

-continued

```
<400> SEQUENCE: 5

Leu Leu Thr Val Glu Gln Ala Leu Ala Asp Phe Ala Glu Leu Leu Arg
1               5                   10                  15

Ala Leu Arg Arg Asp Leu
            20

<210> SEQ ID NO 6
<211> LENGTH: 33
<212> TYPE: PRT
<213> ORGANISM: human

<400> SEQUENCE: 6

His Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val Gly Glu
            20                  25                  30

Arg

<210> SEQ ID NO 7
<211> LENGTH: 33
<212> TYPE: PRT
<213> ORGANISM: human

<400> SEQUENCE: 7

His Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Val

<210> SEQ ID NO 8
<211> LENGTH: 40
<212> TYPE: PRT
<213> ORGANISM: human

<400> SEQUENCE: 8

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu Ala Ala Arg
        35                  40

<210> SEQ ID NO 9
<211> LENGTH: 40
<212> TYPE: PRT
<213> ORGANISM: human

<400> SEQUENCE: 9

His Met Arg Arg Ile Ala Arg Leu Glu Glu Lys Val Lys Thr Leu Lys
1               5                   10                  15

Ala Gln Asn Ser Glu Leu Ala Ser Thr Ala Asn Met Leu Arg Glu Gln
            20                  25                  30

Val Ala Gln Leu Lys Gln Lys Tyr
        35                  40

<210> SEQ ID NO 10
<211> LENGTH: 36
<212> TYPE: PRT
<213> ORGANISM: unknown
```

```
<220> FEATURE:
<221> NAME/KEY: PEPTIDE
<222> LOCATION: (1)..(36)
<223> OTHER INFORMATION: T-20

<400> SEQUENCE: 10

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 11
<211> LENGTH: 38
<212> TYPE: PRT
<213> ORGANISM: unknown
<220> FEATURE:
<221> NAME/KEY: PEPTIDE
<222> LOCATION: (1)..(38)
<223> OTHER INFORMATION: DP107

<400> SEQUENCE: 11

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 12
<211> LENGTH: 34
<212> TYPE: PRT
<213> ORGANISM: unknown
<220> FEATURE:
<221> NAME/KEY: PEPTIDE
<222> LOCATION: (1)..(34)
<223> OTHER INFORMATION: N34

<400> SEQUENCE: 12

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg

<210> SEQ ID NO 13
<211> LENGTH: 28
<212> TYPE: PRT
<213> ORGANISM: unknown
<220> FEATURE:
<221> NAME/KEY: PEPTIDE
<222> LOCATION: (1)..(28)
<223> OTHER INFORMATION: C28

<400> SEQUENCE: 13

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys
            20                  25
```

```
<210> SEQ ID NO 14
<211> LENGTH: 68
<212> TYPE: PRT
<213> ORGANISM: unknown
<220> FEATURE:
<221> NAME/KEY: PEPTIDE
<222> LOCATION: (1)..(68)
<223> OTHER INFORMATION: N34(L6)C28

<400> SEQUENCE: 14

Ser Gly Ile Val Gln Gln Gln Asn Asn Leu Arg Ala Ile Glu Ala
 1               5                  10                  15

Gln Gln His Leu Leu Gln Leu Thr Val Trp Gly Ile Lys Gln Leu Gln
             20                  25                  30

Ala Arg Ser Gly Gly Arg Gly Gly Trp Met Glu Trp Asp Arg Glu Ile
         35                  40                  45

Asn Asn Tyr Thr Ser Leu Ile His Ser Leu Ile Glu Glu Ser Gln Asn
     50                  55                  60

Gln Gln Glu Lys
65

<210> SEQ ID NO 15
<211> LENGTH: 39
<212> TYPE: PRT
<213> ORGANISM: unknown
<220> FEATURE:
<221> NAME/KEY: PEPTIDE
<222> LOCATION: (1)..(39)
<223> OTHER INFORMATION: T1249

<400> SEQUENCE: 15

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
             20                  25                  30

Ala Ser Leu Trp Glu Trp Phe
         35

<210> SEQ ID NO 16
<211> LENGTH: 502
<212> TYPE: PRT
<213> ORGANISM: human immunodeficiency virus

<400> SEQUENCE: 16

Met Arg Val Lys Gly Ile Arg Lys Ser Tyr Gln Tyr Leu Trp Lys Gly
 1               5                  10                  15

Gly Thr Leu Leu Leu Gly Ile Leu Met Ile Cys Ser Ala Val Glu Lys
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ala Tyr Asp Thr Glu Val
     50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                 85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125
```

```
Asn Cys Lys Asp Val Asn Ala Thr Asn Thr Thr Asn Asp Ser Glu Gly
130                 135                 140

Thr Met Glu Arg Gly Glu Ile Lys Asn Cys Ser Phe Asn Ile Thr Thr
145                 150                 155                 160

Ser Ile Arg Asp Glu Val Gln Lys Glu Tyr Ala Leu Phe Tyr Lys Leu
            165                 170                 175

Asp Val Val Pro Ile Asp Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
            245                 250                 255

Leu Leu Asn Gly Ser Leu Ala Glu Glu Val Val Ile Arg Ser Asp
            260                 265                 270

Asn Phe Thr Asn Asn Ala Lys Thr Ile Ile Val Gln Leu Lys Glu Ser
        275                 280                 285

Val Glu Ile Asn Cys Thr Arg Pro Asn Asn Asn Thr Arg Lys Ser Ile
290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
            325                 330                 335

Thr Leu Lys Gln Ile Val Ile Lys Leu Arg Glu Gln Phe Glu Asn Lys
        340                 345                 350

Thr Ile Val Phe Asn His Ser Ser Gly Gly Asp Pro Glu Ile Val Met
    355                 360                 365

His Ser Phe Asn Cys Gly Gly Glu Phe Phe Tyr Cys Asn Ser Thr Gln
370                 375                 380

Leu Phe Asn Ser Thr Trp Asn Asn Asn Thr Glu Gly Ser Asn Asn Thr
385                 390                 395                 400

Glu Gly Asn Thr Ile Thr Leu Pro Cys Arg Ile Lys Gln Ile Ile Asn
            405                 410                 415

Met Trp Gln Glu Val Gly Lys Ala Met Tyr Ala Pro Pro Ile Arg Gly
        420                 425                 430

Gln Ile Arg Cys Ser Ser Asn Ile Thr Gly Leu Leu Leu Thr Arg Asp
    435                 440                 445

Gly Gly Ile Asn Glu Asn Gly Thr Glu Ile Phe Arg Pro Gly Gly Gly
450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
            485                 490                 495

Val Gln Arg Glu Lys Arg
            500

<210> SEQ ID NO 17
<211> LENGTH: 511
<212> TYPE: PRT
<213> ORGANISM: human immunodeficiency virus
```

<400> SEQUENCE: 17

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
            210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
            290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
            370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415
```

-continued

```
Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
            500                 505                 510
```

SULFATED CCR5 PEPTIDES FOR HIV-1 INFECTION

This application is a continuation of U.S. Ser. No. 09/796,202 filed Feb. 28, 2001 now U.S. Pat. No. 6,548,636, which is a continuation-in-part of and claims the benefit under 35 U.S.C. §120 of U.S. Provisional Application No. 60/267,231 filed Feb. 7, 2001, U.S. Provisional application No. 60/205,839, filed May 19, 2000 and U.S. Provisional application No. 60/185,667, filed Feb. 29, 2000, the contents of which are hereby incorporated by reference into this application.

The invention disclosed herein was made with Government support under NIH Grant Nos. R01AI43847 (T.D.) and R01DK54718 (T.P.S.) from the Department of Health and Human Services. Accordingly, the government has certain rights in this invention.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

HIV-1 entry into target cells is mediated by the successive interaction of the envelope glycoprotein gp120 with CD4 and a co-receptor belonging to the seven trans-membrane G protein-coupled chemokine receptor family (Berger et al. Ann. Rev. Immunol. 17:657, 1999). Binding of gp120 to CD4 exposes or creates a co-receptor binding site on gp120 (Trkola et al. Nature 384:184, 1996, Wu et al. Nature, 384:179, 1996). CCR5 and CXCR4 are the most physiologically relevant and widely used HIV-1 co-receptors (Zhang and Moore, J. Virol. 73:3443, 1999). CCR5 mediates the entry of R5 isolates and CXCR4 mediates the entry of X4 isolates. R5X4 isolates are able to exploit both co-receptors (Berger et al., Ann. Rev. Immunol. 17:657, 1999). It has been demonstrated that specific amino acids including acidic residues and tyrosines located within the CCR5 amino-terminal domain (Nt, amino acids 2–31) are essential for CCR5-mediated fusion and entry of R5 and R5X4 HIV-1 strains (Dragic et al. J. Virol. 72:279, 1998; Rabut et al. J. Virol. 72:3464, 1998; Farzan et al. J. Virol. 72:1160, 1998; Dorantz et al. J. Virol. 71:6305, 1997). More recently, Farzan et al. demonstrated that tyrosine residues in the CCR5 Nt are sulfated (Farzan et al. Cell 96:667, 1999)

Inhibition of cellular sulfation pathways, including tyrosine sulfation, by sodium chlorate decreased the binding of a gp120/CD4 complex to CCR5$^+$ cells (Farzan et al. Cell 96:667, 1999). A number of prior reports had implicated a role for sulfate moieties in HIV-1 entry. Several sulfated compounds, such as dextran sulfate, can inhibit HIV-1 entry by associating with CD4 or gp120 (Baeuerle and Huttner J. Cell Biol 105:2655, 1987; Baba et al. Proc. Natl. Acad. Sci. USA 85:6132, 1998). Sulfated proteoglycans have been shown to bind to HIV-1 gp120 at or near its third variable (V3) loop, which also determines co-receptor usage (Roderiquez et al. J. Virol. 69:2233, 1995; Hwang et al. Science 253:71, 1991). It is therefore conceivable that sulfo-tyrosines in the CCR5 Nt also interact with gp120, increasing its affinity for CCR5. The reduction in gp120/CD4 binding caused by the pre-treatment of target cells with sodium chlorate, however, cannot be formally attributed to a reduction in CCR5 tyrosine sulfation since chlorate can inhibit the sulfation of both tyrosines and proteoglycans.

The region of the CCR5 Nt spanning amino acids 2–18 contains residues that are critically important for viral entry (Dragic et al. J. Virol. 72:279, 1998; Rabut et al. J. Virol. 72:3464, 1998; Farzan et al. J. Virol. 72:1160, 1998; Dorantz et al. J. Virol. 71:6305, 1997). We previously demonstrated that tyrosines at positions 3, 10 and 14 were required for optimal co-receptor function, whereas the Tyr15Phe substitution had little effect on entry (Rabut et al. J. Virol. 72:3464, 1998). Taken together, these findings suggested that HIV-1 entry may be critically dependent upon sulfation of Tyr-3, -10 and -14, but not Tyr-15. We therefore explored the role of sulfo-tyrosines in positions 3, 10 and 14 by synthesizing peptides corresponding to amino acids 2–18 of the CCR5 Nt and carrying different tyrosine modifications. We first tested the ability of the Nt peptides to inhibit binding of gp120/CD4 complexes and anti-CCR5 MAbs to CCR5$^+$ cells. The specific association of certain peptides with gp120/sCD4 complexes or with anti-CCR5 MAbs was further confirmed by surface plasmon resonance (BIAcore) analysis. Inhibition of HIV-1 entry by the CCR5 Nt peptides was also tested. Our results suggest that amino acids 2–18 of the CCR5 Nt compose a gp120-binding site that determines the specificity of the interaction between CCR5 and gp120s from R5 and R5X4 isolates. Post-translational sulfation of the tyrosine residues in the CCR5 Nt is required for gp120 binding and may critically modulate the susceptibility of target cells to HIV-1 infection in vivo.

CCR5's normal physiologic activities involve binding and transducing signals mediated by CC-chemokines, including RANTES, MIP-1α and MIP-1β, which direct activation and trafficking of T cells and other inflammatory cells. As such, CCR5 plays an important role in mediating the inflammatory reaction of diseases such as rheumatoid arthritis and multiple sclerosis. The synovial fluid of rheumatoid arthritis patients is highly enriched in CCR5-expressing T cells (Qin et al. J Clin Invest 101:746, 1998), and CCR5 is the predominant CC chemokine receptor expressed on T cells in the rheumatoid synovium (Gomez-Reino et al. Arthritis Rheum 42:989, 1999). Similarly, infiltration by CCR5-expressing cells is characteristic of plaque lesions in patients with multiple sclerosis (Balashov et al. Proc Natl Acad Sci USA 96:6873, 1999) Such observations provide a rationale for the use of agents that block CCR5 for therapy of inflammatory/autoimmune diseases, including but not limited to arthritis, multiple sclerosis, asthma, psoriasis, autoimmune diabetes, transplant rejection, and atherosclerosis.

SUMMARY OF THE INVENTION

This invention provides a compound comprising the structure:

θαYDINYYTSEβλ wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein λ represents a carboxyl group or an amidated carboxyl group; wherein all of α,Y,D,I,N,Y,Y, T,S,E and β are joined together by peptide bonds; further provided that at least two tyrosines in the compound are sulfated.

This invention also provides a compound comprising the structure:

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction; wherein β represents from 0 to 333 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein λ represents a carboxyl group or an amidated carboxyl group; wherein all of α,Y,D,I,N,Y,Y, T,S,E and β are joined together by peptide bonds; further provided that at least two tyrosines in the compound are sulfated.

This invention provides a composition which comprises a carrier and an amount of one of the compounds described herein effective to inhibit binding of HIV-1 to a CCR5 receptor on the surface of a CD4+ cell.

This invention provides a method of inhibiting human immunodeficiency virus infection of a CD4+ cell which also carries a CCR5 receptor on its surface which comprises contacting the CD4+ cell with an amount of one of the compounds described herein effective to inhibit binding of human immunodeficiency virus to the CCR5 receptor so as to thereby inhibit human immunodeficiency virus infection of the CD4+ cell.

This invention provides a method of preventing CD4+ cells of a subject from becoming infected with human immunodeficiency virus which comprises administering to the subject an amount of one of the compounds described herein effective to inhibit binding of human immunodeficiency virus to CCR5 receptors on the surface of the CD4+ cells so as to thereby prevent the subject's CD4+ cells from becoming infected with human immunodeficiency virus.

This invention provides a method of treating a subject whose CD4+ cells are infected with human immunodeficiency virus which comprises administering to the subject an amount of one of the compounds described herein effective to inhibit binding of human immunodeficiency virus to CCR5 receptors on the surface of the subject's CD4+ cells so as to thereby treat the subject.

This invention provides a method of identifying an agent which inhibits binding of a CCR5 ligand to a CCR5 receptor which comprises:
(a) immobilizing one of the compounds described herein on a solid support;
(b) contacting the immobilized compound from step (a) with sufficient detectable CCR5 ligand to saturate all binding sites for the CCR5 ligand on the immobilized compound under conditions permitting binding of the CCR5 ligand to the immobilized compound so as to form a complex;
(c) removing any unbound CCR5 ligand;
(d) contacting the complex from step (b) with the agent; and
(e) detecting whether any CCR5 ligand is displaced from the complex, wherein displacement of detectable CCR5 ligand from the complex indicates that the agent binds to the compound so as to thereby identify the agent as one which inhibits binding of the CCR5 ligand to the CCR5 receptor.

This invention provides a method of identifying an agent which inhibits binding of a CCR5 ligand to a CCR5 receptor which comprises:
(a) contacting one of the compounds described herein with sufficient detectable CCR5 ligand to saturate all binding sites for the CCR5 ligand on the compound under conditions permitting binding of the CCR5 ligand to the compound so as to form a complex;
(b) removing any unbound CCR5 ligand;
(c) measuring the amount of CCR5 ligand which is bound to the compound in the complex;
(d) contacting the complex from step (a) with the agent so as to displace CCR5 ligand from the complex;
(e) measuring the amount of CCR5 ligand which is bound to the compound in the presence of the agent; and
(f) comparing the amount of CCR5 ligand bound to the compound in step (e) with the amount measured in step (c), wherein a reduced amount measured in step (e) indicates that the agent binds to the compound so as to thereby identify the agent as one which inhibits binding of the CCR5 ligand to the CCR5 receptor.

This invention also provides a method of identifying an agent which inhibits binding of a CCR5 ligand to a CCR5 receptor which comprises:
(a) immobilizing one of the compounds described herein on a solid support;
(b) contacting the immobilized compound from step (a) with the agent and sufficient detectable CCR5 ligand to saturate all binding sites for the CCR5 ligand on the compound under conditions permitting binding of the CCR5 ligand to the immobilized compound so as to form a complex;
(c) removing any unbound CCR5 ligand;
(d) measuring the amount of detectable CCR5 ligand which is bound to the immobilized compound in the complex;
(e) measuring the amount of detectable CCR5 ligand which binds to the immobilized compound in the absence of the agent;
(f) comparing the amount of CCR5 ligand which is bound to the immobilized compound in step (e) with the amount measured in step (d), wherein a reduced amount measured in step (d) indicates that the agent binds to the compound so as to thereby identify the agent as one which inhibits binding of the CCR5 ligand to the CCR5 receptor.

This invention also provides a method of identifying an agent which inhibits binding of a CCR5 ligand to a CCR5 receptor which comprises:
(a) contacting one of the compounds described herein with the agent and sufficient detectable CCR5 ligand to saturate all binding sites for the CCR5 ligand on the compound under conditions permitting binding of the CCR5 ligand to the compound so as to form a complex;

(b) removing any unbound CCR5 ligand;

(c) measuring the amount of detectable CCR5 ligand which is bound to the compound in the complex;

(d) measuring the amount of detectable CCR5 ligand which binds to the compound in the absence of the agent;

(e) comparing the amount of CCR5 ligand which is bound to the compound in step (c) with the amount measured in step (d), wherein a reduced amount measured in step (c) indicates that the agent binds to the compound so as to thereby identify the agent as one which inhibits binding of the CCR5 ligand to the CCR5 receptor.

This invention provides a method of identifying an agent which inhibits binding of a CCR5 ligand to a CCR5 receptor which comprises:

a) immobilizing one of the compounds described herein on a solid support;

b) contacting the immobilized compound from step a) with the agent dissolved or suspended in a known vehicle and measuring the binding signal generated by such contact;

c) contacting the immobilized compound from step a) with the known vehicle in the absence of the compound and measuring the binding signal generated by such contact;

d) comparing the binding signal measured in step b) with the binding signal measured in step c), wherein an increased amount measured in step b) indicates that the agent binds to the compound so as to thereby identify the agent as one which binds to the CCR5 receptor.

This invention provides a method of obtaining a composition which comprises:

(a) identifying a compound which inhibits binding of a CCR5 ligand to a CCR5 receptor according to one of the above methods; and (b) admixing the compound so identified or a homolog or derivative thereof with a carrier.

This invention provides a compound having the structure:

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein λ represents a carboxyl group or an amidated carboxyl group; wherein all of α,Y,D,I,N,Y,Y,T,S,E and β are joined together by peptide bonds, further provided that at least two tyrosines in the compound are sulfated, wherein n is an integer from 1 to 8, Δ is a polymer, and the solid line represents up to 8 linkers which attach the structure in parentheses to Δ.

This invention also provides a compound having the structure:

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein all of α,Y,D,I,N,Y,Y,T,S,E and β are joined together by peptide bonds, further provided that at least two tyrosines in the compound are sulfated, wherein n is an integer from 1 to 8, Δ is a polymer, and the solid line represents up to 8 linkers which attach the structure in parentheses to Δ.

This invention provides a compound having the structure:

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 333 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein λ represents a carboxyl group or an amidated carboxyl group; wherein all of α,Y,D,I,N,Y,Y,T,S,E and β are joined together by peptide bonds, further provided that at least two tyrosines in the compound are sulfated, wherein Π is an integer from 1 to 8, Δ is a polymer, and the solid line represents up to 8 linkers which attach the structure in parentheses to Δ.

This invention also provides a compound having the structure:

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction;

wherein β represents from 0 to 333 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein all of α,Y,D,I,N,Y,Y,T,S,E and β are joined together by peptide bonds, further provided that at least two tyrosines in the compound are sulfated, wherein Π is an integer from 1 to 8, Δ is a polymer, and the solid line represents up to 8 linkers which attach the structure in parentheses to Δ.

BRIEF DESCRIPTION OF THE FIGURES

FIG. 1 Effect of peptides on $gp120_{JR-FL}$ binding to CCR5.

L1.2-CCR5$^+$ cells were incubated with the biotinylated $gp120_{JR-FL}$/CD4-IgG2 complex in the presence of different concentration of peptides (a) S-3/10/14, S-10/14, S-10, S-14 or (b) P-3/10/14, P-10/14, SR-2/12, SR-10/14, TS-10/14. The extent of complex binding in the absence of peptide was defined as 100% (m.f.i. ~40±5). Binding in the presence of peptide is expressed as a percentage of control. When CCR5-negative cells were used, binding of the $gp120_{JR-FL}$/CD4-IgG2 complex was negligible (~10%, m.f.i. ~2±1). The values shown are from a representative experiment.

Figure 2:
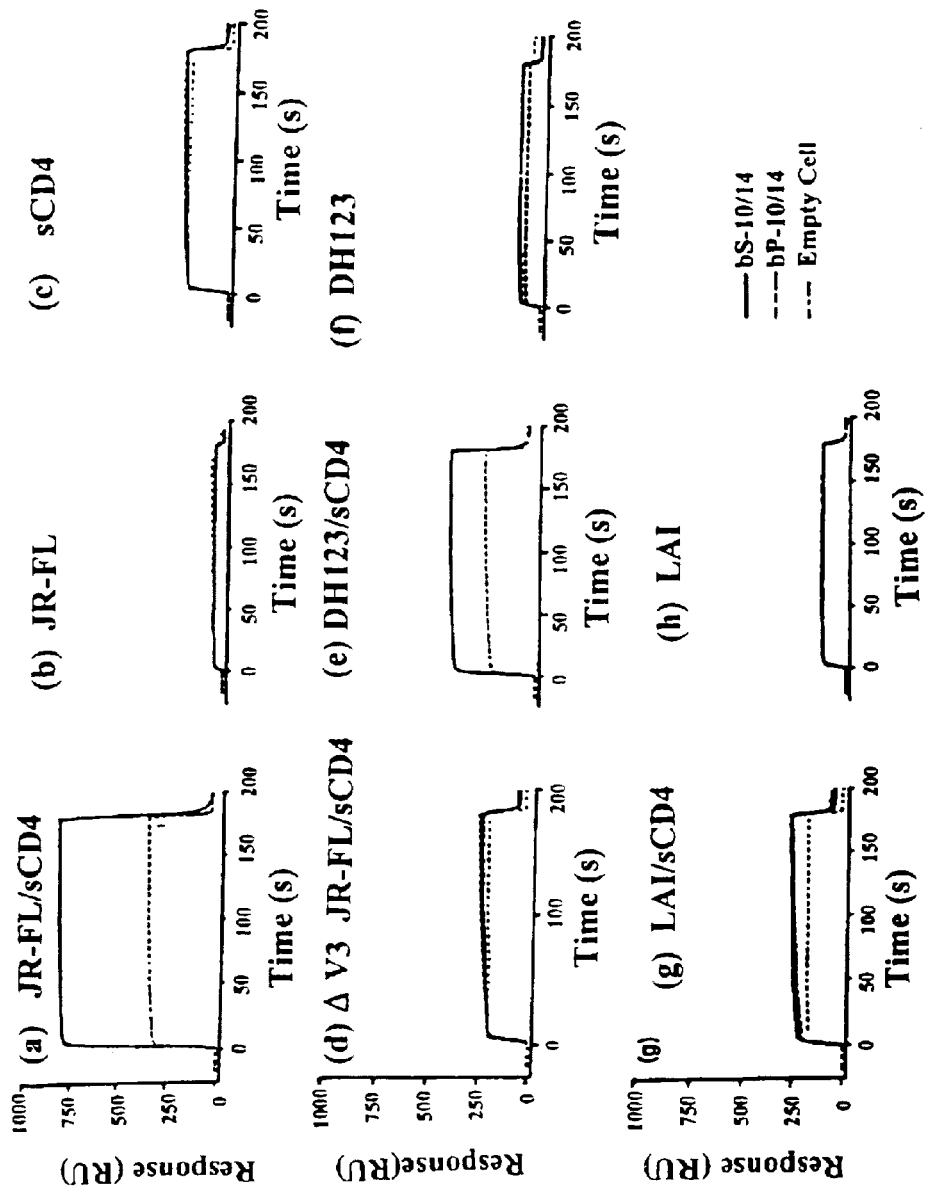

FIG. 2 Binding of the gp120/sCD4 complex to sulfated and phosphorylated peptides.

Biotinylated peptides were immobilized on a sensor chip and their ability to associate with gp120/sCD4 was analyzed by BIAcore. RU values as a function of time were measured in the absence of peptide (gray dotted lines), in the presence of phosphorylated peptide (black dotted lines) or in the presence of sulfated peptide (solid black lines). We performed binding analyses with the following proteins: (a) $gp120_{JR-FL}$/sCD4, (b) $gp120_{JR-FL}$, (c) sCD4, (d) $DV3gp120_{JR-FL}$/sCD4, (e) $gp120_{DH123}$/sCD4, (f) $gp120_{DH123}$, (g) $gp120_{LAI}$/sCD4 and (h) $gp120_{LAI}$.

Figure 3:
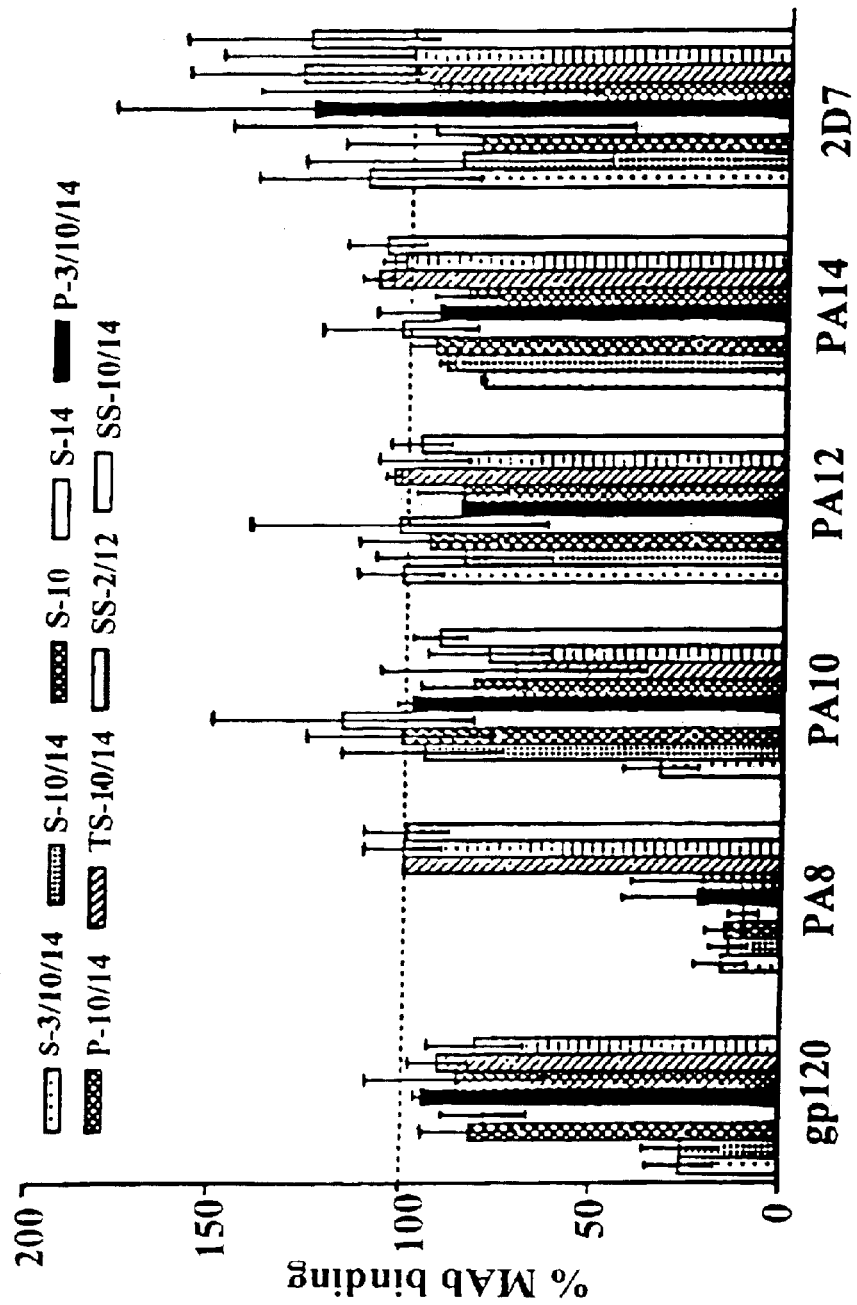

FIG. 3 Effect of peptides on MAb binding to CCR5.

L1.2-CCR5$^+$ cells were incubated with the anti-CCR5 MAbs in the presence of peptides. The extent of MAb binding in the absence of peptide was defined as 100% (m.f.i. ~50–400, depending on the MAb). Binding in the presence of peptide is expressed as a percentage of control. When CCR5-negative cells were used, binding of MAbs was negligible (m.f.i. ~2±1). Each data point represents the mean±s.d. of three replicates.

Figure 4:
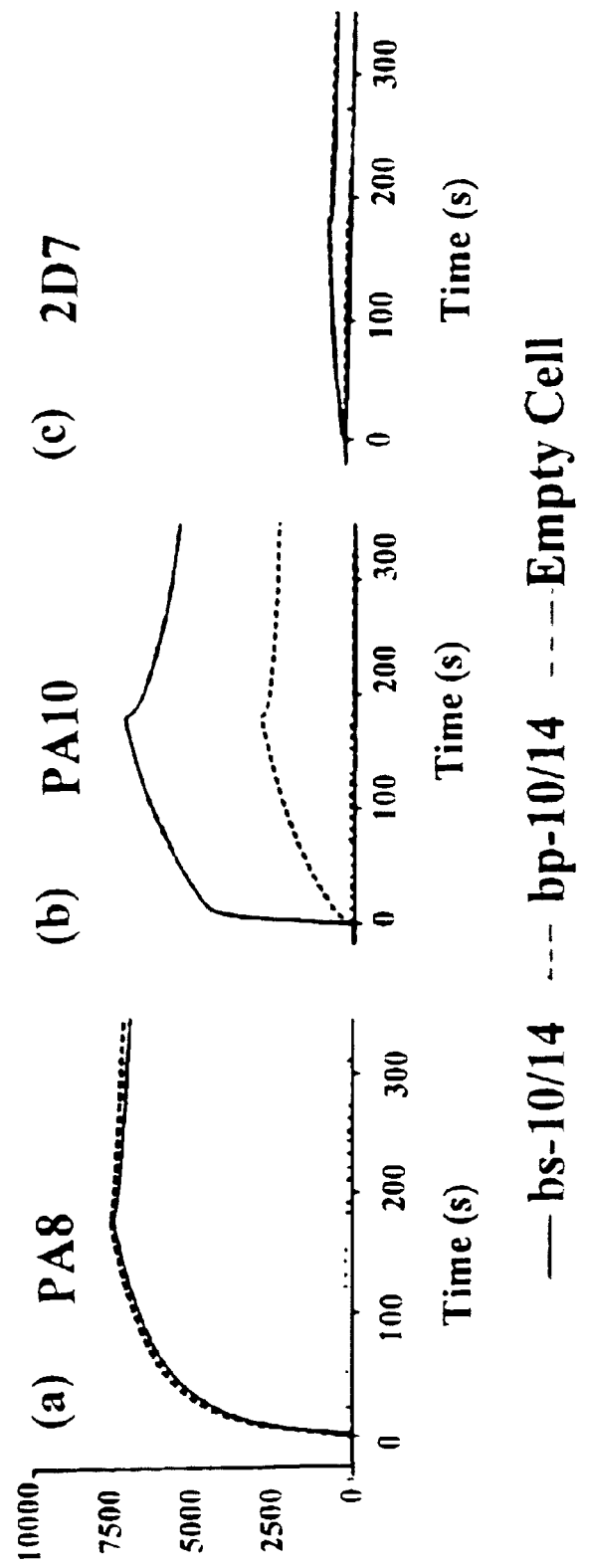

FIG. 4 Binding of MAbs to sulfated and phosphorylated peptides.

Biotinylated peptides were immobilized, on a sensor chip and their ability to associate with anti-CCR5 MAbs was analyzed by BIAcore. RU values as a function of time were measured in the absence of peptide (gray dotted lines), in the presence of phosphorylated peptide (black dotted lines) or in the presence of sulfated peptide (solid black lines). We performed binding analyses with (a) PA8, (b) PA10 and (c) 2D7.

Figure 5:
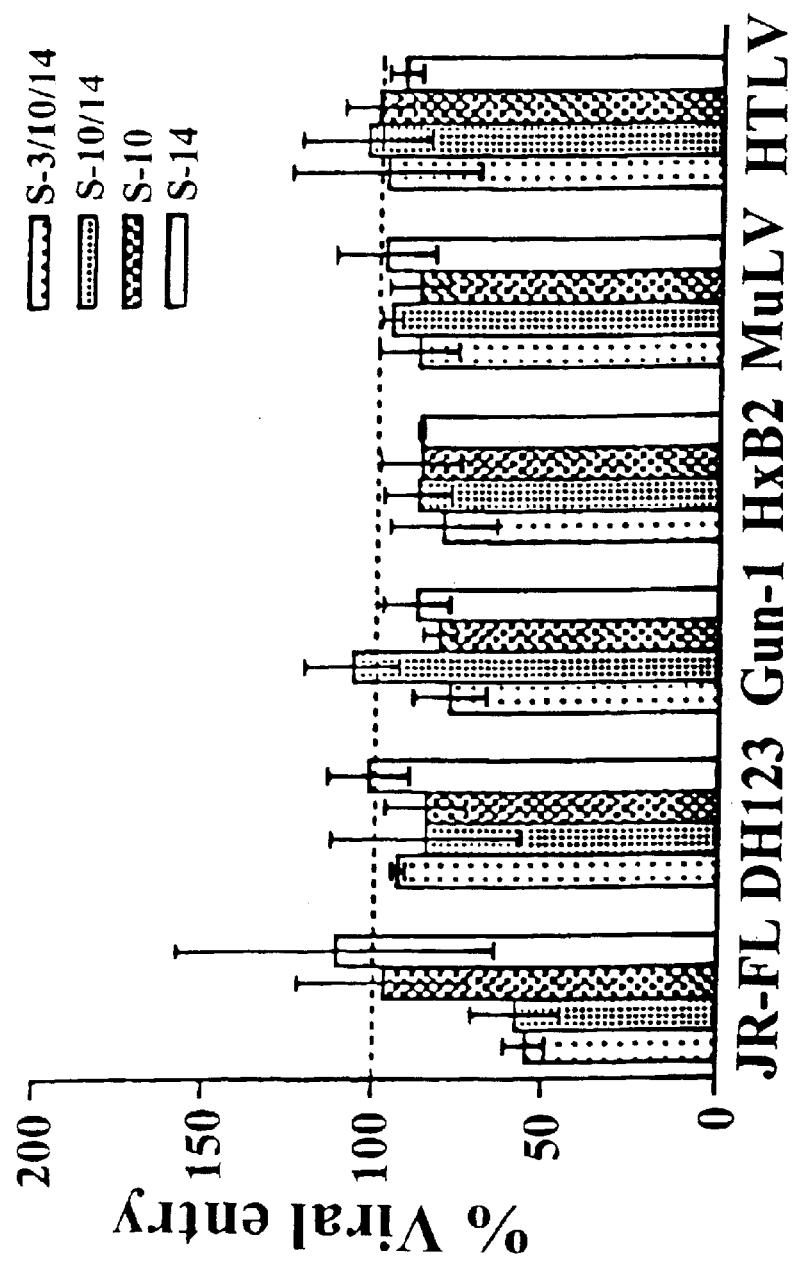

FIG. 5 Effect of peptides on viral entry.

HeLa-CD4$^+$CCR5$^+$ cells were infected with Nlluc$^+$env$^-$ pseudotyped with different viral envelopes in the presence of peptides. Luciferase activity (r.l.u.) was measured 48 h post-infection. The extent of entry in the absence of peptide was defined as 100% (r.l.u. ~25,000±9,000). Background r.l.u. values were ~7±2. Each data point represents the mean±s.d. of three replicates.

FIG. 6 CCR5 Nt peptide sequences and labels

The primary sequence of each peptide is indicated in the left column and the corresponding label is indicated in the right column. Sulfated tyrosine residues are designated by black boxes and white boxes designate phosphorylated tyrosine residues.

Figure 7:
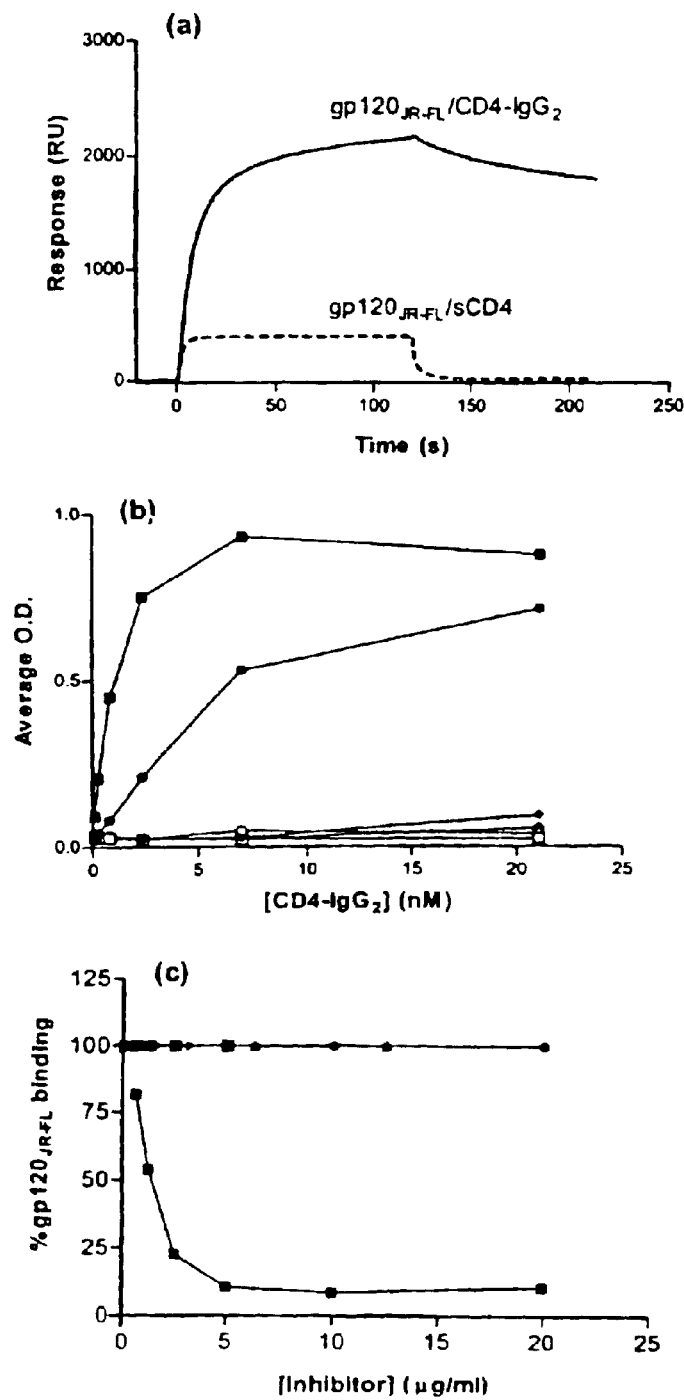

FIG. 7 Gp120/CD4 complex binding to CCR5 Nt sulfopeptides

Peptide 2–18 was bound to streptavidin-coated biosensor chips and $gp120_{JR-FL}$/sCD4 (dotted line) or $gp120_{JR-FL}$/CD4-IgG$_2$ (solid line) were flowed over the sensor chip surface. Resonance units (RU) were measured as a function of time using a Biacore X and reflect complex-peptide binding (a). Sulfopeptide 2–18 (solid symbols) or phosphopeptide 2–18(P) (clear symbols) were immobilized on streptavidin-coated ELISA plates and incubated with gp120/CD4-IgG$_2$ complexes. Gp120 proteins were derived from the R5 isolate JR-FL (squares), the R5X4 isolate DH123 (circles) and the X4 isolate LAI (diamonds). Complexes-peptide binding was detected by an HRP-conjugated goat anti-human IgG antibody. O.D. at 450 nm was measured after addition of HRP substrate and is expressed as a function of CD4-IgG$_2$ concentration (b). Biotinylated sulfopeptide 2–18 was immobilized on streptavidin-coated plates and incubated with gp120/CD4-IgG$_2$ complex in the presence of increasing concentrations of: PA 8 (solid squares), TAK-779 (triangles), Rantes (inverted triangles), MIP-1 (diamonds), MIP-1 (circles) or SDF-1 (clear squares). Binding of the complexes to the peptide was detected by incubation with HRP-conjugated goat anti-human IgG antibody. O.D. at 450 nm was measured after addition of HRP substrate and percentage of binding was expressed as a function of inhibitor concentration.

Figure 8:
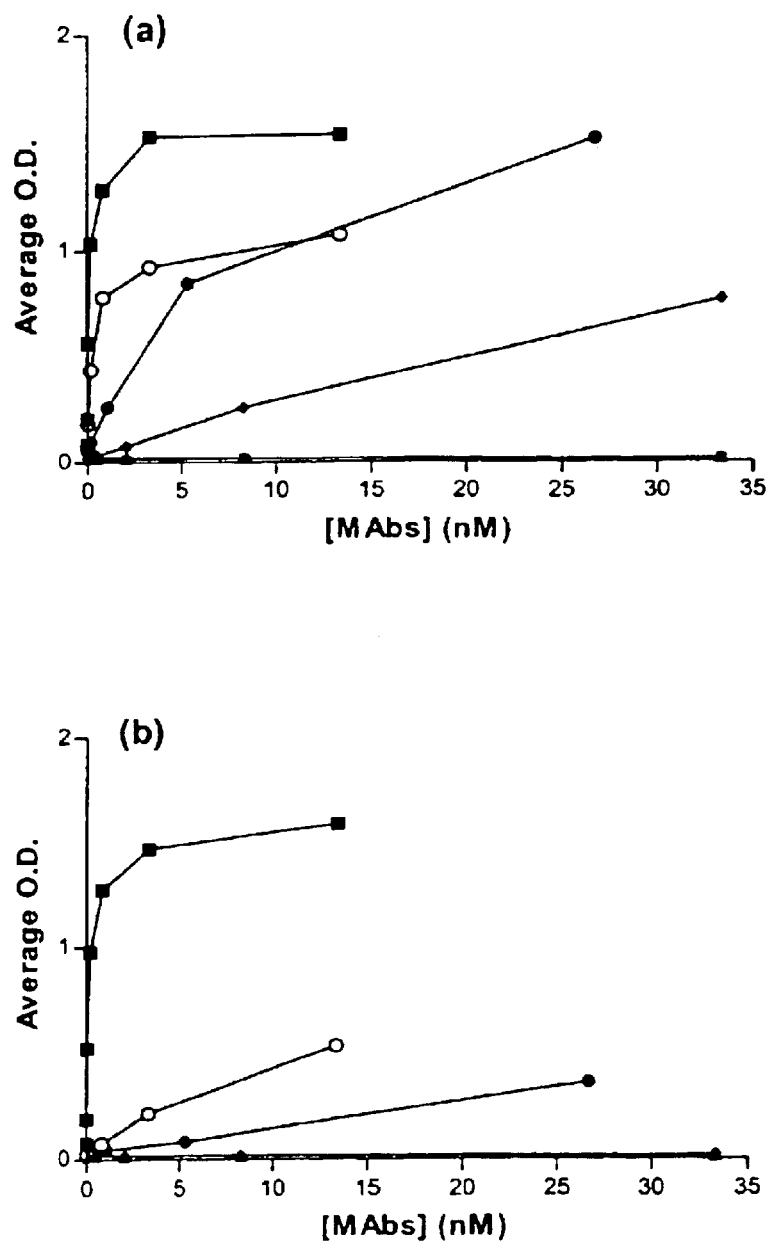

FIG. 8: Binding of anti-CCR5 MAbs to CCR5 Nt peptides.

Sulfopeptides (a) or phosphopeptides (b) were immobilized on streptavidin-coated ELISA plates and incubated with anti-CCR5 MAbs PA8 (solid squares), PA10 (clear circles), PA11 (solid circles), PA12 (solid diamonds) or PA14 (solid triangles). Binding of the MAbs to the peptides was detected by an HRP-conjugated goat anti-mouse IgG antibody. O.D. at 450 nm was measured after addition of HRP substrate and expressed as a function of MAb concentration.

Figure 9:
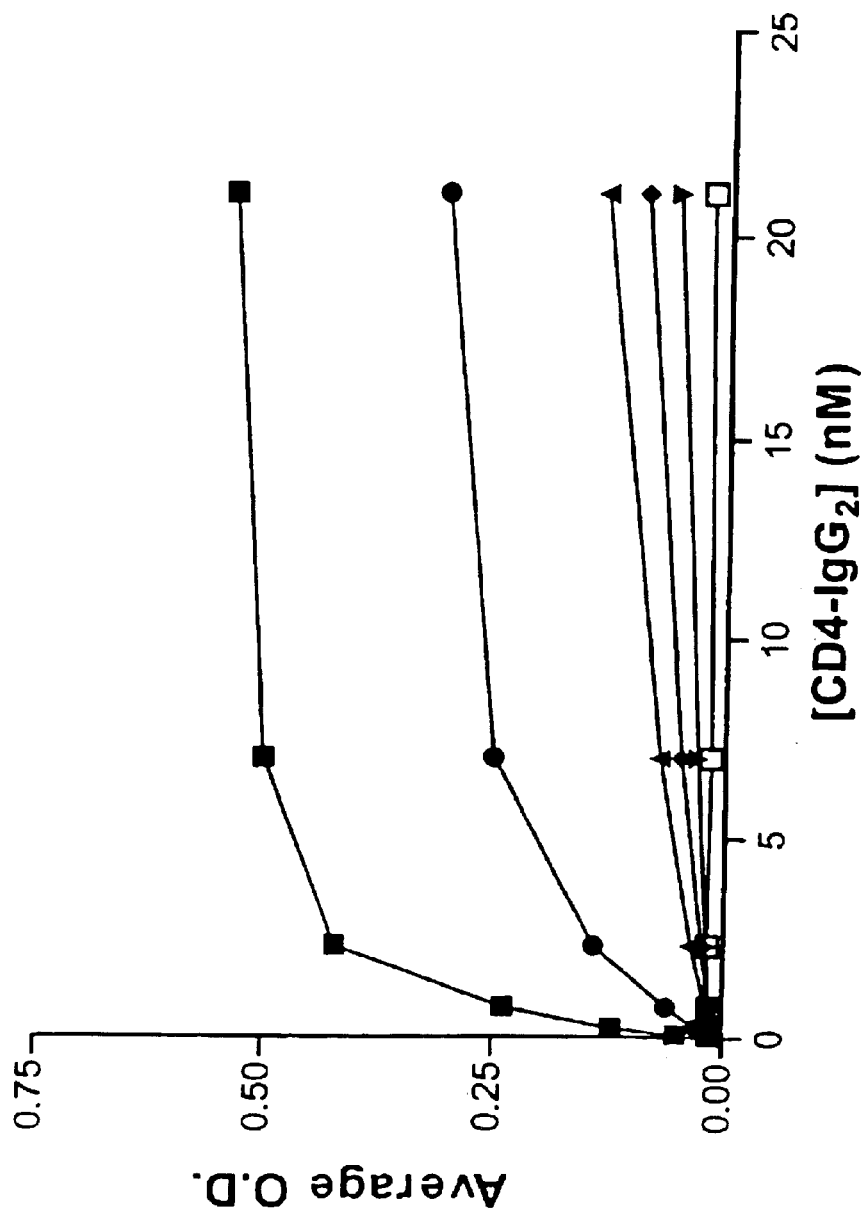

FIG. 9: Binding of $gp120_{JR-FL}$/CD4-IgG$_2$ to different CCR5 Nt-based peptides.

Streptavidin plates were coated with 2–18 (black squares), 10–18 (black circles), 8–15 (black diamonds), 6–16 (black stars), 10–15 (white square), 10–18(11A/18A) (black triangles). Plates were then incubated with $gp120_{JR-FL}$/CD4-IgG$_2$ complex. Binding of the complex to the peptide was detected by an HRP-conjugated goat anti-human IgG antibody. O.D. at 450 nm was measured after addition of HRP substrate and expressed as a function of CD4-IgG$_2$ concentration (nM).

Figure 10:
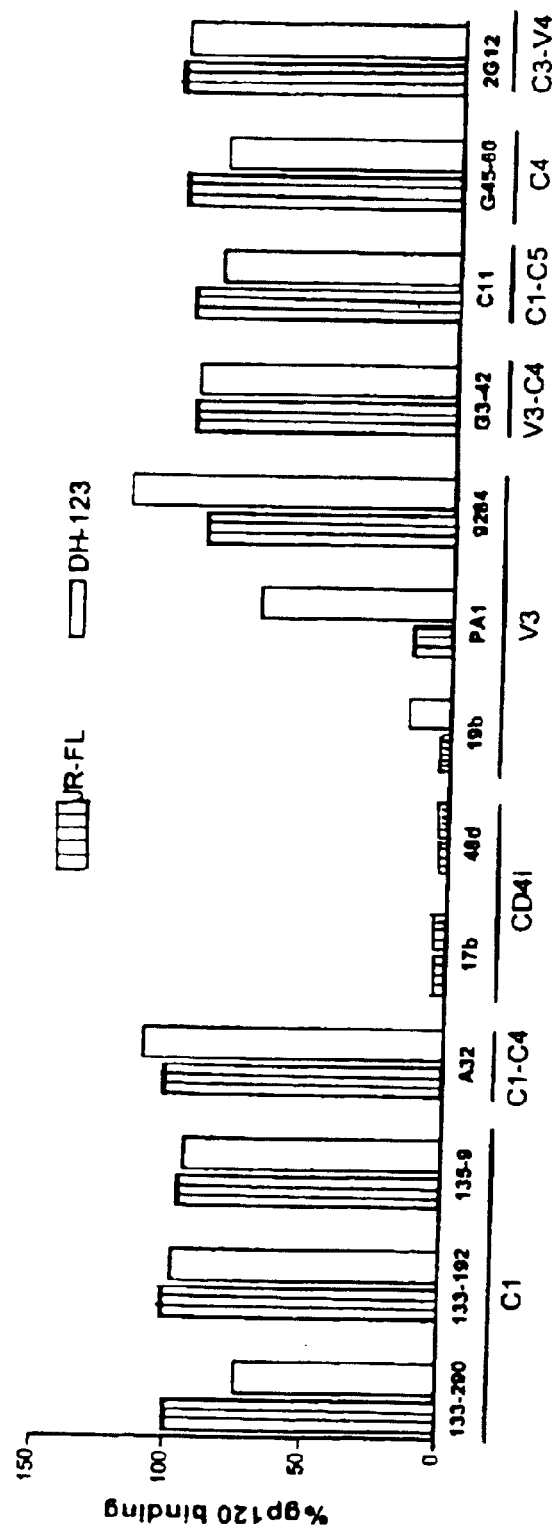

FIG. 10: Inhibition of gp120/CD4-IgG$_2$ complex binding to sulfo-peptides by anti-gp120 MAbs Biotinylated sulfopeptide 2–18 was bound to streptavidin-coated biosensor chips and solutions of either $gp120_{JR-FL}$/CD4-IgG$_2$ complex (black bars) or $gp120_{DH123}$/CD4-IgG$_2$ complex (white bars) were flowed over the surface of the chip in the presence of different anti-gp120 MAbs. The names of the MAbs and the location of their epitopes are indicated along the x-axis. Resonance units (RU) were measured as a function of time using a Biacore X and reflect complex-peptide binding in the presence of the MAbs.

Gp120/CD4-IgG$_2$ binding was calculated using the formula: (RU in the presence of MAbs)/(RU in the absence of MAbs)×100%. The values shown are from a sample experiment.

Figure 11:
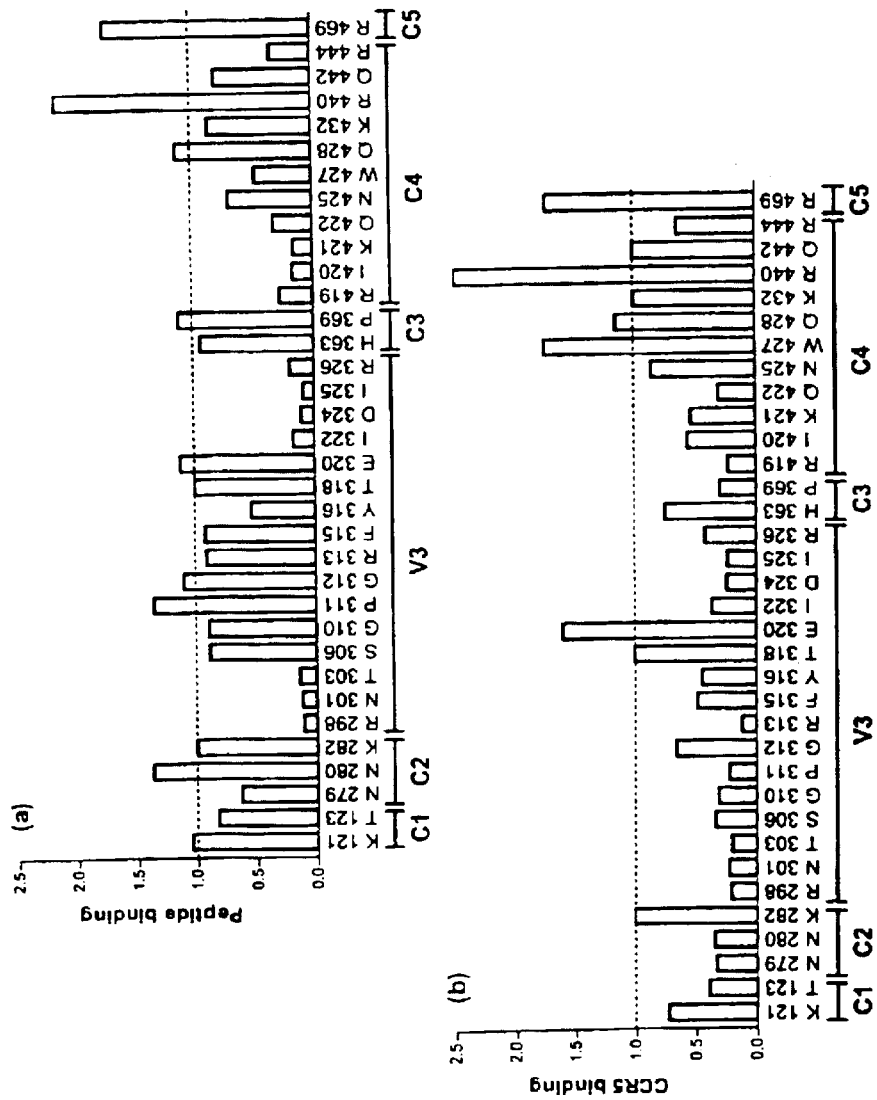

FIG. 11: Binding of gp120 mutants to sulfo-peptide and wild type CCR5.

Sulfo-peptide 2–18 was immobilized on streptavidin-coated plates and incubated with a mixture of gp120-containing supernatants and CD4-IgG$_2$. Peptide-complex binding was detected by an HRP-conjugated goat anti-human IgG antibody. O.D. at 450 nm was measured after addition of HRP substrate and normalized for binding of the gp120 mutants to CD4-IgG$_2$. The doted line represents the normalized value for the binding of the wild type gp120 to the peptide. The mutated amino acids and their locations in gp120 are indicated along the x-axis (a). L12-CCR5$^+$ cells were incubated with a mixture of gp120-containing supernatants and CD4-IgG$_2$. Binding of the complex was detected by FACS analysis after addition of streptavidin-PE. Percentage of gp120/CD4-IgG$_2$ binding to CCR5 was normalized for gp120 binding to CD4-IgG$_2$. The doted line represents the normalized value for the binding of wild-type gp120 to the L12-CCR5$^+$ cells. The mutated amino acids and their locations in gp120 are indicated along the x-axis (b).

FIG. 12: Amino acid sequences of CCR5 Nt-based peptides.

The peptides are named according to the positions of their first and last residues in the full-length sequence of CCR5. They contain either sulfotyrosines (black boxes) or phosphotyrosines (white boxes) n positions 10 and 14. Residues Asp-11 and Glu-18 in peptide 10–18(11A/18A) are substituted for alanines. All peptides carry a carboxy terminal GAG spacer followed by a biotinylated lysine.

FIG. 13: Amino acid conservation among R5 isolates.

Envelope sequences from 25 R5 strains described in the HIV Database and retrieved from the National Center for Biotechnology Information GenBank were aligned and percentage of conservation for the indicated residues was calculated and combined with results from Hung et al., 1999 (REF). Alanine mutants showing more than 50% decrease in sulfopeptide 2–18 binding compared to the wild type are highlighted in gray.

DETAILED DESCRIPTION OF THE INVENTION

The plasmids CD4-IgG2-HC-pRcCMV and CD4-kLC-pRcCMV were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 10801 University Boulevard, Manassas, Va. 20110–2209 under ATCC Accession Nos. 75193 and 75194, respectively.

The plasmids designated PPI4-tPA-gp120$_{JR-FL}$ and PPI4-tPA-gp120$_{LAI}$ were deposited pursuant to, and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110–2209 under ATCC Accession Nos. 75431 and 75432, respectively. These plasmids were deposited with ATCC on Mar. 12, 1993. These eukaryotic shuttle vectors contain the cytomegalovirus major immediate-early (CMV MIE) promoter/enhancer linked to the full-length HIV-1 envelope gene whose signal sequence was replaced with that derived from tissue plasminogen activator. In the vector, a stop codon has been placed at the gp120 C-terminus to prevent translation of gp41 sequences, which are present in the vector. The vector also contains an ampicillin resistance gene, an SV40 origin of replication and a DHFR gene whose transcription is driven by the β-globin promoter.

The monoclonal antibodies PA8, PA10, PA11, PA12, and PA14 were deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Dec. 2, 1998 under the following Accession Nos.: ATCC Accession No. HB-12605 (PA8), ATCC Accession No. HB-12607 (PA10), ATCC Accession No. HB-12608 (PA11), ATCC Accession No. HB-12609 (PA12), and ATCC Accession No. HB-12610 (PA14).

As used herein, the following standard abbreviations are used throughout the specification to indicate specific amino acids:

| | |
|---|---|
| A = ala = alanine | R = arg = arginine |
| N = asn = asparagine | D = asp = aspartic acid |
| C = cys = cysteine | Q = gln = glutamine |
| E = glu = glutamic acid | G = gly = glycine |
| H = his = histidine | I = ile = isoleucine |
| L = leu = leucine | K = lys = lysine |
| M = met = methionine | F = phe = phenylalanine |
| P = pro = proline | S = ser = serine |
| T = thr = threonine | W = trp = tryptophan |
| Y = tyr = tyrosine | V = val = valine |
| B = asx = asparagine or aspartic acid | |
| Z = glx = glutamine or glutamic acid | |

As used herein, the following standard abbreviations are used throughout the specification to indicate specific. nucleotides: C=cytosine; A=adenosine; T=thymidine; G=guanosine; and U=uracil.

This invention provides a compound comprising the structure:

θαYDINYYTSEβλ wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein λ represents a carboxyl group or an amidated carboxyl group; wherein all of α,Y,D,I,N,Y,Y,T,S,E and β are joined together by peptide bonds; further provided that at least two tyrosines in the compound are sulfated.

In one embodiment of the above compound, the compound is peptide which comprises consecutive amino acids having the sequence YDINYYTSE.

In one embodiment of the above compound, the tyrosines at positions 1 and 5 of the sequence YDINYYTSE are sulfated.

In one embodiment of the above compound, α represents less than 9 amino acids. In another embodiment of the above compound, α represents less than 8 amino acids. In another embodiment of the above compound, α represents less than 7 amino acids. In another embodiment of the above compound, α represents less than 6 amino acids. In another embodiment of the above compound, α represents less than 5 amino acids. In another embodiment of the above compound, α represents less than 4 amino acids. In another embodiment of the above compound, α represents less than 3 amino acids. In another embodiment of the above compound, α represents less than 2 amino acids. In another embodiment of the above compound, α represents less than 1 amino acid.

In one embodiment of the above compound, β represents less than 17 amino acids. In one embodiment of the above compound, β represents less than 16 amino acids. In one embodiment of the above compound, β represents less than 15 amino acids. In one embodiment of the above compound, β represents less than 14 amino acids. In one embodiment of the above compound, β represents less than 13 amino acids. In one embodiment of the above compound, β represents less than 12 amino acids. In one embodiment of the above compound, β represents less than 11 amino acids. In one embodiment of the above compound, β represents less than 10 amino acids. In one embodiment of the above compound, β represents less than 9 amino acids. In one embodiment of the above compound, β represents less than 8 amino acids. In one embodiment of the above compound, β represents less than 7 amino acids. In one embodiment of the above compound, β represents less than 6 amino acids. In one embodiment of the above compound, β represents less than 5 amino acids. In one embodiment of the above compound, β represents less than 4 amino acids. In one embodiment of the above compound, β represents less than 3 amino acids. In one embodiment of the above compound, β represents less than 2 amino acids. In one embodiment of the above compound, β represents less than 1 amino acid.

This invention also provides a compound comprising the structure:

θαYDINYYTSEβλ wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction; wherein β represents from 0 to 333 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein λ represents a carboxyl group or an amidated carboxyl group; wherein all of α,Y,D,I,N,Y,Y,T,S,E and β are joined together by peptide bonds; further provided that at least two tyrosines in the compound are sulfated.

In the compounds described herein and as exemplified above, the β in each compound may alternatively represent from 0 to 333 amino acids.

In one embodiment of the compounds described herein, β represents less than 300 amino acids. In another embodiment of the above compound, β represents less than 250 amino acids. In another embodiment of the above compound, β represents less than 200 amino acids. In another embodiment of the above compound, β represents less than 150 amino acids. In another embodiment of the above compound, β represents less than 100 amino acids. In another embodiment of the above compound, β represents less than 75 amino acids. In another embodiment of the above compound, β represents less than 50 amino acids. In another embodiment of the above compound, β represents less than 40 amino acids. In another embodiment of the above compound, β represents less than 35 amino acids. In another embodiment of the above compound, β represents less than 30 amino acids. In another embodiment of the above compound, β represents less than 25 amino acids. In another embodiment of the above compound, β represents less than 20 amino acids. In another embodiment of the above compound, β represents less than 19 amino acids. In another embodiment of the above compound, β represents less than 18 amino acids. In another embodiment of the above compound, β represents less than 17 amino acids. In another embodiment of the above compound, β represents less than 16 amino acids. In another embodiment of the above compound, β represents less than 15 amino acids. In another embodiment of the above compound, β represents less than 14 amino acids. In another embodiment of the above compound, β represents less than 13. amino acids. In another embodiment of the above compound, β represents less than 12 amino acids. In another embodiment of the above compound, β represents less than 11 amino acids.

In one embodiment of the above compound, α represents less than 9 amino acids. In another embodiment of the above compound, α represents less than 8 amino acids. In another embodiment of the above compound, α represents less than 7 amino acids. In another embodiment of the above compound, α represents less than 6 amino acids. In another embodiment of the above compound, α represents less than 5 amino acids. In another embodiment of the above compound, α represents less than 4 amino acids. In another embodiment of the above compound, α represents less than 3 amino acids. In another embodiment of the above compound, α represents less than 2 amino acids. In another embodiment of the above compound, α represents less than 1 amino acid.

The CCR5 amino acid sequence is the following and is set forth in SEQ ID NO:1:

```
  1  MDYQVSSPIYDINYYTSEPCQKINVKQIAARLLPPLYSLV
 41  FIFGFVGNMLVILILINCKRLKSMTDIYLLNLAISDLFFL
 81  LTVPFWAHYAAAQWDFGNTMCQLLTGLYFIGFFSGIFFII
121  LLTIDRYLAVVHAVFALKARTVTFGVVTSVITWVVAVFAS
161  LPGIIFTRSQKEGLHYTCSSHFPYSQYQFWKNFQTLKIVI
201  LGLVLPLLVMVICYSGILKTLLRCRNEKKRHRAVRLIFTI
241  MIVYFLFWAPYNIVLLLNTFQEFFGLNNCSSSNRLDQAMQ
281  VTETLGMTHCCINPIIYAFVGEKFRNYLLVFFQKHIAKRF
321  CKCCSIFQQEAPERASSVYTRSTGEQEISVGL 352
```

The CCR5 nucleotide sequence is the following and is set forth in SEQ ID NO:2:

```
   1  GAATTCCCCC AACAGAGCCA AGCTCTCCAT CTAGTGGACA GGGAAGCTAG CAGCAAACCT
  61  TCCCTTCACT ACAAAACTTC ATTGCTTGGC CAAAAAGAGA GTTAATTCAA TGTAGACATC
 121  TATGTAGGCA ATTAAAAACC TATTGATGTA TAAAACAGTT TGCATTCATG GAGGGCAACT
 181  AAATACATTC TAGGACTTTA TAAAAGATCA CTTTTTATTT ATGCACAGGG TGGAACAAGA
 241  TGGATTATCA AGTGTCAAGT CCAATCTATG ACATCAATTA TTATACATCG GAGCCCTGCC
 301  AAAAAATCAA TGTGAAGCAA ATCGCAGCCC GCCTCCTGCC TCCGCTCTAC TCACTGGTGT
 361  TCATCTTTGG TTTTGTGGGC AACATGCTGG TCATCCTCAT CCTGATAAAC TGCAAAAGGC
 421  TGAAGAGCAT GACTGACATC TACCTGCTCA ACCTGGCCAT CTCTGACCTG TTTTTCCTTC
 481  TTACTGTCCC CTTCTGGGCT CACTATGCTG CCGCCCAGTG GGACTTTGGA AATACAATGT
 541  GTCAACTCTT GACAGGGCTC TATTTTATAG GCTTCTTCTC TGGAATCTTC TTCATCATCC
 601  TCCTGACAAT CGATAGGTAC CTGGCTGTCG TCCATGCTGT GTTTGCTTTA AAAGCCAGGA
 661  CGGTCACCTT TGGGGTGGTG ACAAGTGTGA TCACTTGGGT GGTGGCTGTG TTTGCGTCTC
 721  TCCCAGGAAT CATCTTTACC AGATCTCAAA AAGAAGGTCT TCATTACACC TGCAGCTCTC
 781  ATTTTCCATA CAGTCAGTAT CAATTCTGGA AGAATTTCCA GACATTAAAG ATAGTCATCT
 841  TGGGGCTGGT CCTGCCGCTG CTTGTCATGG TCATCTGCTA CTCGGGAATC CTAAAAACTC
 901  TGCTTCGGTG TCGAAATGAG AAGAAGAGGC ACAGGGCTGT GAGGCTTATC TTCACCATCA
 961  TGATTGTTTA TTTTCTCTTC TGGGCTCCCT ACAACATTGT CCTTCTCCTG AACACCTTCC
1021  AGGAATTCTT TGGCCTGAAT AATTGCAGTA GCTCTAACAG GTTGGACCAA GCTATGCAGG
1081  TGACAGAGAC TCTTGGGATG ACGCACTGCT GCATCAACCC CATCATCTAT GCCTTTGTCG
1141  GGGAGAAGTT CAGAAACTAC CTCTTAGTCT TCTTCCAAAA GCACATTGCC AAACGCTTCT
1201  GCAAATGCTG TTCTATTTTC CAGCAAGAGG CTCCCGAGCG AGCAAGCTCA GTTTACACCC
1261  GATCCACTGG GGAGCAGGAA ATATCTGTGG GCTTGTGACA CGGACTCAAG TGGGCTGGTG
1321  ACCCAGTCAG AGTTGTGCAC ATGGCTTAGT TTTCATACAC AGCCTGGGCT GGGGGT
```

The YDINYYTSE sequence corresponds to amino acid residues 10–18 of the CCR5 sequence set forth above.

As used herein, "CCR5" is a chemokine receptor which binds members of the CC group of chemokines and whose amino acid sequence comprises that provided in Genbank Accession Number 1705896 and related polymorphic variants. The nucleotide sequence comprises that provided in Genbank Accession Number X91492. In one embodiment, the above compound may correspond to the extracellular portion of CCR5. The first 31 amino acids of CCR5 correspond to the extracellular portion of CCR5. Accordingly, the extracellular portion extends from the methionine at position number 1 to the arginine at position number 31 of SEQ ID NO:1. In another embodiment, the above compound may correspond to the amino-terminal portion of CCR5. As used herein, "N-terminus" or amino-terminus means the sequence of amino acids spanning the initiating methionine and the first transmembrane region.

As used herein, "$H_2N$" refers to the N-terminus or amino-terminus. As used herein, "COOH" refers to the C-terminus or carboxy-terminus.

Various tyrosines of the compounds described herein may be sulfated. These include but are not limited to the tyrosines at positions 3, 10 and 14 of amino acid sequence set forth in SEQ ID NO:1. Accordingly, in one embodiment, the tyrosines at positions 10 and 14 are sulfated. In another embodiment, the tyrosines at positions 3 and 14 are sulfated. In another embodiment, the tyrosines at positions 3 and 10 are sulfated. In another embodiment, the tyrosines at positions 3, 10 and 14 are sulfated. Other tyrosines in the sequence set forth in SEQ ID NO:1 may also be sulfated.

This invention provides a composition comprising one of the compounds described herein and a detectable marker attached thereto. In one embodiment of the composition, the detectable marker is biotin. In one embodiment of the composition, the detectable marker is attached at the C-terminus of the compound.

The compounds of the subject invention may also be isolated or purified. In one embodiment the compound is labeled with a detectable marker. As used herein, chemical "labels" include radioactive isotopes, fluorescent groups and affinity moieties such as biotin that facilitate detection of the labeled peptide. Other chemical labels are well-known to those skilled in the art. Methods for attaching chemical labels to peptides are well-known to the skilled artisan.

As used herein, "peptide" and "polypeptide" are used to denote two or more amino acids linked by a peptidic bond between the α-carboxyl group of one amino acid and the α-amino group of the next amino acid. Peptides may be produced by solid-phase synthetic methods that are well-known to those skilled in the art. In addition to the above set of twenty amino acids that are used for protein synthesis in vivo, peptides may contain additional amino acids, including but not limited to hydroxyproline, sarcosine, and γ-carboxyglutamate. The peptides may contain modifying groups including but not limited to sulfate and phosphate moieties. Peptides can be comprised of L- or D-amino acids, which are mirror-image forms with differing optical properties. Peptides containing D-amino acids have the advantage of being less susceptible to proteolysis in vivo.

Peptides may by synthesized in monomeric linear form, cyclized form or as oligomers such as branched multiple antigen peptide (MAP) dendrimers (Tam et al. Biopolymers 51:311, 1999). Nonlinear peptides may have increased binding affinity by virtue of their restricted conformations and/or oligomeric nature. Peptides may also be produced using recombinant methods as either isolated peptides or as a portion of a larger fusion protein that contains additional amino acid sequences.

Peptides may be chemically conjugated to proteins by a variety of well-known methods. Such peptide-protein conjugates can be formulated with a suitable adjuvant and administered parenterally for the purposes of generating polyclonal and monoclonal antibodies to the peptides of interest. Alternatively, unconjugated peptides can be formulated with adjuvant and administered to laboratory animals for the purposes of generating antibodies. Methods for generating and isolating such antibodies are well-known to those skilled in the art.

This invention provides derivatives of the above compound. As used herein, a "derivative" peptide is one whose amino acid sequence is nonidentical to the reference peptide but which possesses functionally similar binding properties. Derivative peptides may also contain N-terminal, C-terminal and/or internal insertions, deletions, or substitutions of amino acids, with the proviso that such insertions, deletions and substitutions do not abrogate the binding properties of the peptide. Derivative peptides include peptides modified with chemical labels to facilitate detection. Derivative peptides include branched and cyclized peptides.

As used herein, "sulfopeptides" are peptides that contain sulfate moieties attached to one or more amino acids, such as tyrosine. In "sulfo-tyrosines", a sulfate group replaces the para-hydroxyl group located on tyrosine side-chain.

As used herein, "phosphopeptides" are peptides that contain phosphate moieties attached to one or more amino acids, such a tyrosine. In "phospho-tyrosines", a phosphate group replaces the para-hydroxyl group located on tyrosine side-chain.

The peptides of the subject invention may be sulfated when synthesized or they may be subsequently sulfated. For example, means of sulfating the peptides include chemical sulfation or enzymatic sulfation. One skilled in the art would know how to employ these and other techniques to sulfate the compound.

This invention provides a composition which comprises a carrier and an amount of one of the compounds described herein effective to inhibit binding of HIV-1 to a CCR5 receptor on the surface of a CD4+ cell.

The carriers include but are not limited to an aerosol, intravenous, oral or topical carrier. Accordingly. The invention provides the above composition adapted for aerosol, intravenous, oral or topical application.

This invention provides the above compositions and a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

As used herein, "composition" means a mixture. The compositions include but are not limited to those suitable for oral, rectal, intravaginal, topical, nasal, opthalmic, or parenteral administration to a subject. As used herein, "parenteral" includes but is not limited to subcutaneous, intravenous, intramuscular, or intrasternal injections or infusion techniques.

As used herein, "administering" may be effected or performed using any of the methods known to one skilled in the art. The methods may comprise intravenous, intramuscular or subcutaneous means. As used herein, "effective dose" means an amount in sufficient quantities to either treat the subject or prevent the subject from becoming infected with HIV-1. A person of ordinary skill in the art can perform simple titration experiments to determine what amount is required to treat the subject.

This invention provides a method of inhibiting human immunodeficiency virus infection of a CD4+ cell which also carries a CCR5 receptor on its surface which comprises contacting the CD4+ cell with an amount of one of the compounds described herein effective to inhibit binding of human immunodeficiency virus to the CCR5 receptor so as to thereby inhibit human immunodeficiency virus infection of the CD4+ cell. As used herein, "inhibits" means that the amount is reduced. In a preferred embodiment, inhibits means that the amount is reduced 100%.

In one embodiment of this method, the CD4+ cell is present in a subject and the contacting is effected by administering the compound to the subject.

This invention provides a method of preventing CD4+ cells of a subject from becoming infected with human immunodeficiency virus which comprises administering to the subject an amount of one of the compounds described herein effective to inhibit binding of human immunodeficiency virus to CCR5 receptors on the surface of the CD4+ cells so as to thereby prevent the subject's CD4+ cells from becoming infected with human immunodeficiency virus.

This invention provides a method of treating a subject whose CD4+ cells are infected with human immunodeficiency virus which comprises administering to the subject an amount of one of the compounds described herein effective to inhibit binding of human immunodeficiency virus to CCR5 receptors on the surface of the subject's CD4+ cells so as to thereby treat the subject.

As used herein, human immunodeficiency virus includes but is not limited to HIV-1, which is the human immunodeficiency virus type-1. HIV-1 includes but is not limited to extracellular virus particles and the forms of HIV-1 found in HIV-1 infected cells.

As used herein, "HIV-1 infection" means the introduction of HIV-1 genetic information into a target cell, such as by fusion of the target cell membrane with HIV-1 or an HIV-1 envelope glycoprotein+ cell. The target cell may be a bodily cell of a subject. In the preferred embodiment, the target cell is a bodily cell from a human subject.

As used herein, "inhibiting HIV-1 infection" means the reduction of the amount of HIV-1 genetic information introduced into a target cell population as compared to the amount that would be introduced without the composition.

In the above methods, the compound may be administered by various routes including but not limited to aerosol, intravenous, oral or topical route. The administration may comprise intralesional, intraperitoneal, intramuscular or intravenous injection; infusion; liposome-mediated delivery; topical, intrathecal, gingival pocket, per rectum, intrabronchial, nasal, oral; ocular or optic delivery. In a further embodiment, the administration includes intrabronchial administration, anal, intrathecal administration or transdermal delivery. In another embodiment, the compound is administered hourly, daily, weekly, monthly or annually. In another embodiment, the effective amount of the compound comprises from about 0.000001 mg/kg body weight to about 100 mg/kg body weight.

The administration may be constant for a certain period of time or periodic and at specific intervals. The compound may be delivered hourly, daily, weekly, monthly, yearly (e.g. in a time release form) or as a one time delivery. The delivery may be continuous delivery for a period of time, e.g. intravenous delivery.

The carrier may be a diluent, an aerosol, a topical carrier, an aqueous solution, a nonaqueous solution or a solid carrier.

The effective amount of the compound may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount.

The compound of the present invention may be delivered locally via a capsule which allows sustained release of the agent or the peptide over a period of time. Controlled or sustained release compositions include formulation in lipophilic depots (e.g., fatty acids, waxes, oils). Also comprehended by the invention are particulate compositions coated with polymers (e.g., poloxamers or poloxamines) and the agent coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

In one embodiment of the above methods, the subject is infected with HIV-1 prior to administering the compound to the subject. In one embodiment of the above methods, the subject is not infected with HIV-1 prior to administering the compound to the subject. In one embodiment of the above methods, the subject is not infected with, but has been exposed to, human immunodeficiency virus.

In one embodiment of the above methods, the effective amount of the compound comprises from about 1.0 ng/kg to about 100 mg/kg body weight of the subject. In another embodiment of the above methods, the effective amount of the compound comprises from about 100 ng/kg to about 50 mg/kg body weight of the subject. In another embodiment of the above methods, the effective amount of the compound comprises from about 1 $\mu$g/kg to about 10 mg/kg body weight of the subject. In another embodiment of the above methods, the effective amount of the compound comprises from about 100 $\mu$g/kg to about 1 mg/kg body weight of the subject.

The dose of the composition of the invention will vary depending on the subject and upon the particular route of administration used. Dosages can range from 0.1 to 100,000 $\mu$g/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming infected with HIV-1. A person of ordinary skill in the art can perform simple titration experiments to determine what amount is required to treat the subject.

In one embodiment of the above method, the subject is a human being. As used herein, "subject" means any animal or artificially modified animal capable of becoming HIV-infected. Artificially modified animals include, but are not limited to, SCID mice with human immune systems. The subjects include but are not limited to mice, rats, dogs, guinea pigs, ferrets, rabbits, and primates. In the preferred embodiment, the subject is a human being.

This invention provides a vaccine which comprises the compound described herein. Vaccines comprising the sulfopeptides and a suitable adjuvant could be administered to a subject for the purposes of generating antibodies or other immune responses that are of therapeutic or prophylactic value. For example, the vaccines could be administered for the purpose of generating in the subject antibodies that bind CCR5 and inhibit its ability to mediate HIV entry and infection, thereby protecting the subject from HIV infection or disease progression. The vaccines may also comprise a suitable adjuvant. The vaccine may also comprises a suitable carrier.

The subject invention has various applications which includes HIV treatment such as treating a subject who has become afflicted with HIV. As used herein, "afflicted with HIV-1" means that the subject has at least one cell which has been infected by HIV-1. As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1. Another application of the subject invention is to prevent a subject from contracting HIV. As used herein, "contracting HIV-1" means becoming infected with HIV-1, whose genetic information replicates in and/or incorporates into the host cells. Another application of the subject invention is to treat a subject who has become infected with HIV-1. As used herein, "HIV-1 infection" means the introduction of HIV-1 genetic information into a target cell, such as by fusion of the target cell membrane with HIV-1 or an HIV-1 envelope glycoprotein$^+$ cell. The target cell may be a bodily cell of a subject. In the preferred embodiment, the target cell is a bodily cell from a human subject. Another application of the subject invention is to inhibit HIV-1 infection. As used herein, "inhibiting HIV-1 infection" means reducing the amount of HIV-1 genetic information introduced into a target cell population as compared to the amount that would be introduced without said composition.

This invention provides a method of identifying an agent which inhibits binding of a CCR5 ligand to a CCR5 receptor which comprises:
(a) immobilizing one of the compounds described herein on a solid support;
(b) contacting the immobilized compound from step (a) with sufficient detectable CCR5 ligand to saturate all binding sites for the CCR5 ligand on the immobilized compound under conditions permitting binding of the CCR5 ligand to the immobilized compound so as to form a complex;
(c) removing any unbound CCR5 ligand;
(d) contacting the complex from step (b) with the agent; and
(e) detecting whether any CCR5 ligand is displaced from the complex, wherein displacement of detectable CCR5 ligand from the complex indicates that the agent binds to the compound so as to thereby identify the agent as one which inhibits binding of the CCR5 ligand to the CCR5 receptor.

This invention provides a method of identifying an agent which inhibits binding of a CCR5 ligand to a CCR5 receptor which comprises:
(a) contacting one of the compounds described herein with sufficient detectable CCR5 ligand to saturate all binding sites for the CCR5 ligand on the compound under conditions permitting binding of the CCR5 ligand to the compound so as to form a complex;
(b) removing any unbound CCR5 ligand;
(c) measuring the amount of CCR5 ligand which is bound to the compound in the complex;
(d) contacting the complex from step (a) with the agent so as to displace CCR5 ligand from the complex;
(e) measuring the amount of CCR5 ligand which is bound to the compound in the presence of the agent; and
(f) comparing the amount of CCR5 ligand bound to the compound in step (e) with the amount measured in step (c), wherein a reduced amount measured in step (e) indicates that the agent binds to the compound so as to thereby identify the agent as one which inhibits binding of the CCR5 ligand to the CCR5 receptor.

This invention also provides a method of identifying an agent which inhibits binding of a CCR5 ligand to a CCR5 receptor which comprises:
(a) immobilizing one of the compounds described herein on a solid support;
(b) contacting the immobilized compound from step (a) with the agent and detectable CCR5 ligand under conditions permitting binding of the CCR5 ligand to the immobilized compound so as to form a complex;
(c) removing any unbound CCR5 ligand;
(d) measuring the amount of detectable CCR5 ligand which is bound to the immobilized compound in the complex;
(e) measuring the amount of detectable CCR5 ligand which binds to the immobilized compound in the absence of the agent;
(f) comparing the amount of CCR5 ligand which is bound to the immobilized compound in step (e) with the amount measured in step (d), wherein a reduced amount measured in step (d) indicates that the agent binds to the compound so as to thereby identify the agent as one which inhibits binding of the CCR5 ligand to the CCR5 receptor.

In one embodiment of the above method, the amount of the detectable CCR5 ligand in step (a) and step (e) is sufficient to saturate all binding sites for the CCR5 ligand on the compound.

This invention also provides a method of identifying an agent which inhibits binding of a CCR5 ligand to a CCR5 receptor which comprises:
(a) contacting one of the compounds described herein with the agent and detectable CCR5 ligand under conditions permitting binding of the CCR5 ligand to the compound so as to form a complex;
(b) removing any unbound CCR5 ligand;
(c) measuring the amount of detectable CCR5 ligand which is bound to the compound in the complex;
(d) measuring the amount of detectable CCR5 ligand which binds to the compound in the absence of the agent;
(e) comparing the amount of CCR5 ligand which is bound to the compound in step (c) with the amount measured in step (d), wherein a reduced amount measured in step (c) indicates that the agent binds to the compound so as to thereby identify the agent as one which inhibits binding of the CCR5 ligand to the CCR5 receptor.

In one embodiment of the above method, the amount of the detectable CCR5 ligand in step (a) and step (d) is sufficient to saturate all binding sites for the CCR5 ligand on the compound.

In one embodiment of the above method the solid support is a microtiter plate well. In another embodiment, the solid support is a bead. In a further embodiment, the solid support is a surface plasmon resonance sensor chip. The surface plasmon resonance sensor chip can have pre-immobilized streptavidin. In one embodiment, the surface plasmon resonance sensor chip is a BIAcore™ chip.

In one embodiment of the above methods, the detectable CCR5 ligand is labeled with a detectable marker. In another embodiment of the above methods, the CCR5 ligand is detected by contacting it with another compound which is both capable of detecting the CCR5 ligand and is detectable. The detectable markers include those described above.

This invention provides a method of identifying an agent which inhibits binding of a CCR5 ligand to a CCR5 receptor which comprises:
a) immobilizing one of the compounds described herein on a solid support;
b) contacting the immobilized compound from step a) with the agent dissolved or suspended in a known vehicle and measuring the binding signal generated by such contact;
c) contacting the immobilized compound from step a) with the known vehicle in the absence of the compound and measuring the binding signal generated by such contact;
d) comparing the binding signal measured in step b) with the binding signal measured in step c), wherein an increased amount measured in step b) indicates that the agent binds to the compound so as to thereby identify the agent as one which binds to the CCR5 receptor.

In one embodiment of the above method, the solid support is a surface plasmon resonance sensor chip. In another embodiment of the above method, the binding signal is measured by surface plasmon resonance.

This invention provides a method of obtaining a composition which comprises:
(a) identifying a compound which inhibits binding of a CCR5 ligand to a CCR5 receptor according to one of the above methods; and
(b) admixing the compound so identified or a homolog or derivative thereof with a carrier.

The invention provides agents identified in the screen. Such agents may have utility in treating HIV-1 infection or other CCR5-mediated diseases, which include rheumatoid arthritis, asthma, multiple sclerosis, psoriasis, atherosclerosis and other inflammatory diseases.

In one embodiment of the above methods, the CCR5 ligand is a complex comprising an HIV-1 envelope glycoprotein and a CD4-based protein. The HIV-1 envelope glycoproteins include but are not limited to gp120, gp140 or gp160. The CD4-based proteins include but are not limited to soluble CD4 or CD4-IgG2.

As used herein, "CD4" means the mature, native, membrane-bound CD4 protein comprising a cytoplasmic domain, a hydrophobic transmembrane domain, and an extracellular domain that binds to the HIV-1 gp120 envelope glycoprotein. As used herein, "HIV-1 envelope glycoprotein" means the HIV-1 encoded protein which comprises the gp120 surface protein, the gp41 transmembrane protein and oligomers and precursors thereof. As used herein, "CD4-based protein" means any protein comprising at least one sequence of amino acid residues corresponding to that portion of CD4 which is required for CD4 to form a complex with the HIV-1 gp120 envelope glycoprotein. As used herein, "CD4-IgG2" means a heterotetrameric CD4-human IgG2 fusion protein encoded by the expression vectors deposited under ATCC Accession Numbers 75193 and 75194.

In one embodiment of the above methods, the CCR5 ligand is a chemokine. The chemokines include but are not limited to RANTES, MIP-1α or MIP-1β. As used herein, "RANTES", "MIP-1α", and "MIP-1β" denote members of the chemokine superfamily of proteins that direct the activation and migration of leukocytes and other cells involved in the inflammation. RANTES, MIP-1α and MIP-1β are known to bind CCR5 and induce signaling. Their peptide sequences have been described (Wells et al. J. Leukocyte Biology, 59:53–60, 1996).

In one embodiment of the above methods, the CCR5 ligand is an antibody. In one embodiment, the antibody is PA8 (ATCC Accession No. HB-12605). In another embodiment, the antibody is PA10 (ATCC Accession No. 12607). In another embodiment, the antibody is PA11 (ATCC Accession No. HB-12608). In another embodiment, the antibody is PA12 (ATCC Accession No. HB-12609).

This invention provides a compound having the structure:

$$\Delta\text{-}(\alpha\text{YDINYYTSE}\beta\lambda)_\Pi$$

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein λ represents a carboxyl group or an amidated carboxyl group; wherein all of α,Y,D,I,N,Y,Y,T,S,E and β are joined together by peptide bonds, further provided that at least two tyrosines in the compound are sulfated, wherein Π is an integer from 1 to 8, Δ is a polymer, and the solid line represents up to 8 linkers which attach the structure in parentheses to Δ.

This invention also provides a compound having the structure:

$$(\theta\alpha\text{YDINYYTSE}\beta)_\Pi\text{-}\Delta$$

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein all of α,Y,D,I,N,Y,Y,T,S,E and β are joined together by peptide bonds,
further provided that at least two tyrosines in the compound are sulfated, wherein Π is an integer from 1 to 8, Δ is a polymer, and the solid line represents up to 8 linkers which attach the structure in parentheses to Δ.

This invention provides a compound having the structure:

$$\Delta\text{-}(\alpha\text{YDINYYTSE}\beta\lambda)_\Pi$$

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 333 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein λ represents a carboxyl group or an amidated carboxyl group; wherein all of α,Y,D,I,N,Y,Y,T,S,E and β are joined together by peptide bonds, further provided that at least two tyrosines in the compound are sulfated, wherein Π is an integer from 1 to 8, Δ is a polymer, and the solid line represents up to 8 linkers which attach the structure in parentheses to Δ.

This invention also provides a compound having the structure:

$$(\theta\alpha\text{YDINYYTSE}\beta)_\Pi\text{-}\Delta$$

wherein each T represents a threonine, each S represents a serine, each E represents a glutamic acid, each Y represents a tyrosine; each D represents an aspartic acid, each I represents an isoleucine; and each N represents an asparagine; wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction; wherein β represents from 0 to 333 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction; wherein θ represents an amino group or an acetylated amino group; wherein all of α,Y,D,I,N,Y,Y,T,S,E and β are joined together by peptide bonds, further provided that at least two tyrosines in the compound are sulfated, wherein Π is an integer from 1 to 8, Δ is a polymer, and the solid line represents up to 8 linkers which attach the structure in parentheses to Δ.

The polymer of the above compounds includes but is not limited to the following: a linear lysine polymer; a branched lysine polymers; a linear arginine polymer; a branched arginine polymer; and polyethylene glycol (PEG), a linear acetylated lysine polymer, a branched acetylated lysine polymer, a linear chloroacetylated lysine polymer and a branched chloroacetylated lysine polymer.

The above compounds can be produced by various methods known to those skilled in the art, including but not limited to the following. Methods for producing synthetic multimeric peptides such as multiple antigen peptides, synthetic polymeric constructs, and branched lysine oligopeptides are well known to those skilled in the art (Spetzler and Tam, Int. J. Pept. Prot. Res. 45:78, 1995; Yai et al., J. Virol., 69:320, 1995; Okuda et al., J. Mol. Recognit. 6:101, 1993). For example, radially branched peptides can be produced by performing standard solid-phase peptide synthesis methods using branched lysine skeletons on 4-(oxy-methyl)-phenylactamidomethyl or other suitable solid resin. Peptide chains are elongated in parallel in a stepwise fashion using optimized t-butyloxycarbonyl/benzyl chemistry as described (Sabatier et al., Biochemistry 32:2763, 1993). Peptides are liberated from the resin, purified by reversed-phase chromatography over a C18 or other suitable column and characterized by analytical HPLC and mass spectroscopy. In another approach, monomeric peptides are synthesized, purified, and then covalently coupled to lysine copolymers using N-succinimidyl maleimido carboxylate chemistry. In another approach, the peptides can also be made in the form of affinity type multimers. For example, peptides may be synthesized with an affinity tag such as biotin. These affinity tagged peptides can then be mixed with affinity ligands capable of binding multimerically, such as streptravidin. Other site-specific ligation chemistries are known to the skilled artisan.

This invention provides a compound comprising the structure:

wherein each E represents a glutamic acid, each D represents an aspartic acid, and each Y represents a tyrosine;
wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction;
wherein β represents from 0 to 13 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction;
wherein θ represents an amino group or an acetylated amino group; wherein λ represents a carboxyl group or an amidated carboxyl group;
wherein Π represents any amino acid,
wherein all of α,Y,D,Π,Π,Y,Π,Π,Π,E and β are joined together by peptide bonds;
further provided that at least two tyrosines in the compound are sulfated.

In one embodiment of this compound, the compound comprises amino acids in addition to those in the YDΠΠΠYΠΠΠΠE peptide, and such amino acids correspond to those present in the CCR5 receptor sequence set forth in SEQ ID NO:1, yet an amino acid may be replaced with a homologous amino acid. The sequence YDΠΠΠYΠΠΠΠE corresponds to amino acid residues 10–18 of the sequence set forth in SEQ ID NO:1. For example, if the peptide has one additional amino acid on its N terminal end, then the sequence could be IYDΠΠΠYΠΠΠΠE or alternatively, the I could be replaced with G, A, V or L.

In one embodiment of the above compound, the compound is a peptide which comprises consecutive amino acids having the sequence YDΠΠΠYΠΠΠΠE.

In one embodiment of the above compound, the tyrosines at positions 1 and 5 of the sequence YDΠΠΠYΠΠΠΠE are sulfated.

As used herein, "homologous amino acids" are those which have chemically similar side chains. For example, aliphatic side chains (G, A, V, L and I); aromatic side chains (F, Y and W); basic aide chains (K, R and H); acidic side chains (D and E); amide side chains (N and Q); aliphatic hydroxyl-containing side chains (S and T); sulfur-containing side chains (C and M). Homology between amino acids may also be drawn on other bases, such as size, polarity, hydrogen bonding potential, hydrophilicity and hydrophobicity. Proline differs from the above amino acids in that it contains a secondary rather than primary imino group. Accordingly, proline may be considered an imino group. Substitution or proline with another amino acid (e.g. G, A or S) can increase the flexibility of a peptide. Conversely, substitution of another amino acid with a proline can stabilize a desired conformation.

This invention provides a compound comprising the structure:

wherein each T represents a threonine, each S represents a serine, each E represents a glutamic acid, each Y represents a tyrosine; each D represents an aspartic acid, each I represents an isoleucine; and each N represents an asparagine;
wherein α represents from 0 to 9 amino acids, with the proviso that if there are more than 2 amino acids, they are joined by peptide bonds in consecutive order and have a sequence identical to the sequence set forth in SEQ ID NO: 1 beginning with the I at position 9 and extending therefrom in the amino terminal direction;

wherein β represents from 0 to 13 amino acids, with the proviso that if there are more than 2 amino acids, they are joined by peptide bonds in consecutive order and have a sequence identical to the sequence set forth in SEQ ID NO: 1 beginning with the P at position 19 and extending therefrom in the carboxy terminal direction;

wherein θ represents an amino group or an acetylated amino group; wherein λ represents a carboxyl group or an amidated carboxyl group;

wherein all of α,Y,D,I,N,Y,Y,T,S,E and β are joined together by peptide bonds;

further provided that at least two tyrosines in the compound are sulfated, wherein any amino acid except for the Y at position 1, D at position 2, Y at position 5 and E at position 9 may be replaced with a homologous amino acid.

In one embodiment of the above compound, with respect to replacing homologous amino acids, any I amino acid residue may be replaced with a G,A,V or L amino acid residue. In one embodiment of the above compound, any N amino acid residue may be replaced with a Q amino acid residue. In one embodiment of the above compound, any Y amino acid residue may be replaced with a F or W amino acid residue. In one embodiment of the above compound, any T amino acid residue may be replaced with a S amino acid residue. In one embodiment of the above compound, any S amino acid residue may be replaced with a T amino acid residue. In one embodiment of the above compound, any C may be replaced with M,S,T,A,G,N, or Q.

In one embodiment, a C amino acid residue within the β region of the compound may be replaced with any other amino acid.

This invention provides an agent which binds to an epitope of HIV-1 gp120, which epitope comprises amino acid residues R298, N301, T303, I322, D324, I325, R326, I420, K421, Q422, W427, thereby inhibiting binding of HIV-1 gp120 to a CCR5 chemokine receptor.

The above amino acid numbering is per HIV-1 strain HxB2 (Genbank Accession No. AAB50262). Amino acids D324, I325 and R326 are derived from HIV-1 strain JR-FL (Genbank Accession No. AAB05604).

The amino acid sequence (SEQ ID NO:17) for HIV-1 HxB2 gp120 is set forth below:

```
  1 MRVKEKYQHL WRWGWRWGTM LLGMLMICSA TEKLWVTVYY GVPVWKEATT TLFCASDAKA
 61 YDTEVHNVWA THACVPTDPN PQEVVLVNVT ENFNMWKNDM VEQMHEDIIS LWDQSLKPCV
121 KLTPLCVSLK CTDLKNDTNT NSSSGRMIME KGEIKNCSFN ISTSIRGKVQ KEYAFFYKLD
181 IIPIDNDTTS YKLTSCNTSV ITQACPKVSF EPIPIHYCAP AGFAILKCNN KTFNGTGPCT
241 NVSTVQCTHG IRPVVSTQLL LNGSLAEEEV VIRSVNFTDN AKTIIVQLNT SVEINCTRPN
301 NNTRKRIRIQ RGPGRAFVTI GKIGNMRQAH CNISRAKWNN TLKQIASKLR EQFGNNKTII
361 FKQSSGGDPE IVTHSFNCGG EFFYCNSTQL FNSTWFNSTW STEGSNNTEG SDTITLPCRI
421 KQIINMWQKV GKAMNYAPPIS GQIRCSSNIT GLLLTRDGGN SNNESEIFRP GGGDMRDNWR
481 SELYKYKVVK IEPLGVAPTK AKRRVVQREK R
```

The amino acid sequence (SEQ ID NO:16) for HIV-1 JR-FL gp120 is set forth below:

```
  1 MRVKGIRKSY QYLWKGGTLL LGILMICSAV EKLWVTVYYG VPVWKEATTT LFCASDAKAY
 61 DTEVHNVWAT HACVPTDPNP QEVVLENVTE HFNMWKNNMV EQMQEDIISL WDQSLKPCVK
121 LTPLCVTLNC KDVNATNTTN DSEGTMERGE IKNCSFNITT SIRDEVQKEY ALFYKLDVVP
181 IDNNNTSYRL ISCDTSVITQ ACPKISFEPI PIHYCAPAGF AILKCNDKTF NGKGPCKNVS
241 TVQCTHGIRP VVSTQLLLNG SLAEEEVVIR SDNFTNNAKT IIVQLKESVE INCTRPNNNT
301 RKSIHIGPGR AFYTTGEIIG DIRQAHCNIS RAKWNDTLKQ IVIKLREQFE NKTIVFNHSS
361 GGDPEIVMHS FNCGGEFFYC NSTQLFNSTW NNNTEGSNNT EGNTITLPCR IKQIINMWQE
421 VGKAMYAPPI RGQIRCSSNI TGLLLTRDGG INENGTEIFR PGGGDMRDNW RSELYKYKVV
481 KIEPLGVAPT KAKRRVVQRE KR
```

This invention provides the above agent, wherein the epitope is altered or masked by an alanine substitution of at least one of the amino acid residues R298, N301, T303, I322, D324, I325, R326, I420, K421, Q422 and W427.

This invention provides an agent which binds to an epitope of HIV-1 gp120, which epitope comprises amino acid residues R298, N301, T303, I322, D324, I325, R326, I420, K421, Q422, W427, thereby inhibiting HIV-1 infection of a CD4+ CCR5+ cell.

This invention provides the above agent, wherein the epitope is altered or masked by an alanine substitution of at least one of the amino acid residues R298, N301, T303, I322, D324, I325, R326, I420, K421, Q422 and W427.

In one embodiment of any of the above agents, the agent is a peptide. In one embodiment of any of the above agents, the peptide comprises consecutive amino acids having the sequence YDINYYTSE. In one embodiment at least two tyrosines in the compound are sulfated. In one embodiment, the tyrosines at positions 1 and 5 of the sequence YDINYYTSE are sulfated.

In one embodiment of any of the above agents, the agent is an antibody or portion of an antibody. In one embodiment of any of the above agents, the agent is a nonpeptidyl agent. In one embodiment of any of the above agents, the agent is a peptidyl agent.

This invention provides a method of inhibiting HIV-1 infection of a CD4+CCR5+ cell which comprises contacting the cell with an amount of an agent of the subject invention effective to bind to HIV-1 gp120, so as to thereby inhibit HIV-1 infection of the CD4+ CCR5+ cell.

This invention provides a compound having one of the following structures:

Δ-(αYDINYYTSEβλ), (θαYDINYYTSEβ)-Δ, or Δ-(αYDINYYTSEβ)-Δ

- wherein each T represents a threonine, each S represents a serine, each E represents a glutamic acid, each Y represents a tyrosine; each D represents an aspartic acid, each I represents an isoleucine; and each N represents an asparagine;
- wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction;
- wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction;
- wherein λ represents a carboxyl group or an amidated carboxyl group;
- wherein θ represents an amino group or an acetylated amino group;
- wherein all of α,Y,D,I,N,Y,Y,T,S,E and β are joined together by peptide bonds,
- further provided that at least two tyrosines in the compound are sulfated,
- wherein Δ is a molecule that self-oligomerizes, and the solid line represents a peptide linker or a peptide, disulfide, or other chemical bond.

As used herein "peptide linker" is a peptide comprising consecutive amino acids having a sequence which includes but is not limited to GAG, SGGRGG and QSTRGGASGGG or repeating units thereof. One skilled in the art would know other flexible peptide linkers.

In one embodiment of the above compound, the peptide that self-oligomerizes contains alpha-helical regions capable of forming coiled coils.

The α-helical coiled coil (48) is probably the most widespread subunit oligomerization motif found in proteins (48–52). It is a type of protein structure consisting of two to five amphipathic α-helixes that "coil" around each other in a left-handed supertwist (48–52). The sequences of coiled are characterized by a heptad repeat of seven residues with a hydrophobic repeat of mostly apolar amino acids.

In one embodiment of the above compound, the peptide that self-oligomerizes is a peptide having a sequence of at least a portion HIV-1 gp41 heptad repeat sequence 1. In one embodiment, the HIV-1 gp41 heptad repeat sequence 1 is RQLLSGIVQQQNNLL-RAIEAQQHLLQLTVWGIKQLQARILAVERYLKDQ (SEQ ID NO:3).

In one embodiment of the above compound, the peptide that self-oligomerizes is a peptide having a sequence of at least a portion of an HIV-1 gp41 heptad repeat sequence 2. In one embodiment, the HIV-1 gp41 heptad repeat sequence 2 is WMEWDREINNYTSLIHSLIEESQN-QQEKNEQELLE (SEQ ID NO:4).

In one embodiment of the above compound, the peptide that self-oligomerizes is a peptide having a sequence corresponding to at least a portion of the leucine zipper region of transcription factor GCN4. In one embodiment, the sequence of the leucine zipper region of transcription factor GCN4 is HMKQLEDKVEELLSKNYHLENE-VARLKKLVGER (SEQ ID NO:6).

In one embodiment of the above compound, the peptide that self-oligomerizes is a peptide having a sequence corresponding to at least a portion of the leucine zipper region of transcription factor GCN4. In one embodiment, the sequence is derived from the leucine zipper region of transcription factor GCN4. In one embodiment, the sequence forms trimeric coiled-coils. In one embodiment, the sequence is HMKQIEDKIEEILSKIYHIENE-IARIKKLIGEV (SEQ ID NO:7).

In one embodiment of the above compound, the peptide that self-oligomerizes is a peptide having a sequence corresponding to at least a portion of a leucine zipper region of a human protein. The human protein includes but is riot limited to transcription activator c-fos, transcription activator c-jun, enzyme quiescent cell proline dipeptidase, macrophage scavenger receptor, salivary mucin (MUC7), or human quiescent cell proline dipeptidase (QPP). In one embodiment, the human protein is QPP and the leucine zipper region has the sequence LLTVEQALADFAELL-RALRRDL (SEQ ID NO:5). In one embodiment, the transcription activator is c-fos and the leucine zipper region has the sequence LTDTLQAETDQLEDEKSALQTEIAN-LLKEKEKLEFILAAR (SEQ ID NO:8). In one embodiment, the transcription activator is c-jun and the leucine zipper region has the, sequence HMRRIAR-LEEKVKTLKAQNSELASTANMLREQVAQLKQKY (SEQ ID NO:9).

In one embodiment of the above compound, the peptide that self-oligomerizes is a peptide having a sequence corresponding to that of at least a portion of an antibody. In one embodiment, the portion of the antibody comprises the heavy chain. In one embodiment, the portion of the antibody heavy chain comprises the heavy chain constant region. In one embodiment, the portion of the antibody heavy chain comprises the hinge and Fc domains. In one embodiment, the portion of the antibody heavy chain comprises the Fc domain. In one embodiment, the portion of the antibody comprises the light chain. In one embodiment, the portion comprises the light chain constant region. In one embodiment, the portion of the antibody comprises the heavy and light chains.

This invention provides a compound having one of the following structures:

Δ-(αYDINYYTSEβλ), (θαYDINYYTSEβ)-Δ, or
Δ-(αYDINYYTSEβ)-Δ wherein each T represents a threonine, each S represents a serine, each E represents a glutamic acid, each Y represents a tyrosine; each D represents an aspartic acid, each I represents an isoleucine; and each N represents an asparagine;

wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction;

wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction;

wherein λ represents a carboxyl group or an amidated carboxyl group;

wherein θ represents an amino group or an acetylated amino group;

wherein all of α,Y,D,I,N,Y,Y,T,S,E and β are joined together by peptide bonds, further provided that at least two tyrosines in the compound are sulfated, wherein Δ is toxin, and the solid line represents a peptide linker or a peptide, disulfide, or other chemical bond.

In one embodiment of the above compound, the toxin is a radionuclide. In one embodiment, the radionuclide is an alpha-emitting isotope. The alpha-emitting isotope includes but is not limited to $^{225}Ac$, $^{211}At$, $^{212}Bi$, or $^{213}Bi$. In one embodiment, the radionuclide is a beta-emitting isotope. The beta-emitting isotope includes but is not limited to $^{186}Rh$, $^{188}Rh$ $^{90}Y$, $^{131}I$, or $^{67}Cu$. In one embodiment, the radionuclide may be emitting Auger and low energy electron. The radionuclide includes but is not limited to $^{131}I$, $^{125}I$ or $^{77}Br$.

In one embodiment of the above compound, the toxin is a chemical toxin. The chemical toxin may be a peptidyl chemical toxin. The peptidyl chemical toxin includes but is not limited to ricin. The chemical toxin may be a nonpeptidyl chemical toxin. The nonpeptidyl chemical toxin includes but is not limited to calicheamycin.

This invention provides a compound having one of the following structures:

Δ-(αYDINYYTSEβλ), (θαYDINYYTSEβ)-Δ, or
Δ-(αYDINYYTSEβ)-Δ, wherein each T represents a threonine, each S represents a serine, each E represents a glutamic acid, each Y represents a tyrosine; each D represents an aspartic acid, each I represents an isoleucine; and each N represents an asparagine;

wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction;

wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction;

wherein λ represents a carboxyl group or an amidated carboxyl group;

wherein θ represents an amino group or an acetylated amino group;

wherein all of α,Y,D,I,N,Y,Y,T,S,E and β are joined together by peptide bonds, further provided that at least two tyrosines in the compound are sulfated, wherein Δ is molecule with anti-HIV activity, and the solid line represents a peptide linker or a peptide, disulfide, or other chemical bond.

In one embodiment of the above compound, the molecule with anti-HIV activity is a CD4-immunoglobulin fusion protein. In one embodiment, the CD4-immunoglobulin fusion protein is CD4-IgG2, wherein the CD4-IgG2 comprises two heavy chains and two lights chains, wherein the heavy chains are encoded by an expression vector designated CD4-IgG2HC-pRcCMV (ATCC Accession No. 75193) and the light chains are encoded by an expression vector designated CD4-kLC-pRcCMV (ATCC Accession No. 75194).

In one embodiment of the above compound, the molecule with anti-HIV activity is a compound which retards gp41 from adopting a conformation capable of mediating fusion of HIV-1 to a CD4+ cell by binding noncovalently to an epitope on a gp41 fusion intermediate. In one embodiment, the compound comprises a peptide selected from the group consisting of T-20 (SEQ ID NO: 10), DP107 (SEQ ID NO: 11), N34 (SEQ ID NO: 12), C28 (SEQ ID NO: 13), N34 (L6) C28 (SEQ ID NO: 14), and T1249 (SEQ ID NO:15).

As used herein, "T-20" and "DP178" are used interchangeably to denote a peptide having the following amino acid sequence: YTSLIHSLIEESQNQQEKNEQELLELDK-WASLWNWF (SEQ ID NO:10) and as described [53,54].

DP107 has the following amino acid sequence:

NNLLRAIEAQQHLLQLTVWGIKQLQA-RILAVERYLKDQ (SEQ ID NO:11)

N34 has the following amino acid sequence:

SGIVQQQNNLLRAIEAQQHLLQLTVWGIKQLQAR (SEQ ID NO:12)

C28 has the following amino acid sequence:

WMEWDREINNYTSLIHSLIEESQNQQEK (SEQ ID NO:13)

N34(L6)C28 has the following amino acid sequence:

SGIVQQQNNLL-RAIEAQQHLLQLTVWGIKQLQARSGGRG-GWMEWDREINNYTSLIHSL IEESQNQQEK (SEQ ID NO:14)

T1249 has the following amino acid sequence:

WQEWEQKITALLEQA-QIQQEKNEYELQKLDKWASLWEWF (SEQ ID NO:15)

This invention provides the above compound wherein the molecule with anti-HIV activity is a CCR5 chemokine receptor targeting agent.

In one embodiment, the CCR5 chemokine receptor targeting agent is an antibody or portion of an antibody. In one embodiment, the antibody includes but is not limited to PA8

(ATCC Accession No. HB-12605), PA10 (ATCC Accession No. 12607), PA11 (ATCC Accession No. HB-12608), PA12 (ATCC Accession No. HB-12609), and PA14 (ATCC Accession No. HB-12610). In one embodiment, the antibody is PA14 (ATCC Accession No. HB-12610).

The antibody may be a monoclonal antibody or polyclonal antibody. The monoclonal antibody may be a human, humanized or chimeric antibody. This invention provides humanized forms-of the above antibodies.

As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody, i.e., in the present invention, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 (55) comprise the production of chimeric antibodies having a variable region of one antibody and a constant region of another antibody.

U.S. Pat. No. 5,225,539 (56) describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 (57) and 5,693,761 (58) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (59) also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 Å of the CDRs in a three dimensional model of the antibody and is predicted to be capable of interacting with the CDRs. The above methods are merely illustrative of some of the methods that one skilled in the art could employ to make humanized antibodies.

This invention provides the above compound, wherein the portion of the antibody is a Fab fragment of the antibody. This invention provides the above compound, wherein the portion of the antibody comprises the variable domain of the antibody. This invention provides the above compound, wherein the portion of the antibody comprises a complementary determining region or CDR portion of the antibody. The monoclonal antibody includes but is not limited to an IgG, IgM, IgD, IgA, or IgE monoclonal antibody.

This invention provides the above compound, wherein the molecule with anti-HIV activity is a chemokine or chemokine derivative. The chemokine includes but is not limited to RANTES, MIP-1$\alpha$, MIP-1$\beta$, SDF-1 or other chemokine which blocks HIV-1 infection. The chemokine derivative includes but is not limited to Met-RANTES, AOP-RANTES, RANTES 9–68, or NNY-RANTES.

The molecule may also be a non-chemokine agent capable of binding to chemokine receptors and inhibiting fusion of HIV-1 to $CD4^+$ cells. The non-chemokine agents include, but are not limited to, chemokine fragments and chemokine derivatives and analogues. In one embodiment, the agent does not include naturally occurring chemokines. The non-chemokine agents include multimeric forms of the chemokine fragments and chemokine derivatives and analogues or fusion molecules which contain chemokine fragments, derivatives and analogues linked to other molecules. In one embodiment, the non-chemokine agents do not include bicyclams and their derivatives as described in U.S. Pat. No. 5,021,409, issued Jun. 4, 1991, the content of which is incorporated by reference into this application. Some bicyclam derivatives have been previously described with antiviral activities (60, 61).

In an embodiment of this invention, the non-chemokine agent is an oligopeptide. In another embodiment, the non-chemokine agent is a polypeptide. In still another embodiment, the non-chemokine agent is an antibody or a portion thereof. Antibodies against the chemokine receptor may easily be generated by routine experiments. It is also within the level of ordinary skill to synthesize fragments of the antibody capable of binding to the chemokine receptor. In a further embodiment, the non-chemokine agent is a nonpeptidyl agent such as TAK-779 (64) or AMD3100 (65).

Non-chemokine agents which are purely peptidyl in composition can be either chemically synthesized by solid-phase methods (62) or produced using recombinant technology in either prokaryotic or eukaryotic systems. The synthetic and recombinant methods are well known in the art.

Non-chemokine agents which contain biotin or other nonpeptidyl groups can be prepared by chemical modification of synthetic or recombinant chemokines or non-chemokine agents. One chemical modification method involves periodate oxidation of the 2-amino alcohol present on chemokines or non-chemokine agents possessing serine or threonine as their N-terminal amino acid (63). The resulting aldehyde group can be used to link peptidyl or non-peptidyl groups to the oxidized chemokine or non-chemokine agent by reductive amination, hydrazine, or other chemistries well known to those skilled in the art.

This invention provides a compound having one of the following structures:

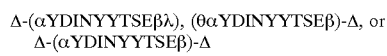

wherein each T represents a threonine, each S represents a serine, each E represents a glutamic acid, each Y represents a tyrosine; each D represents an aspartic acid, each I represents an isoleucine; and each N represents an asparagine;

wherein α represents from 0 to 9 amino acids, with the proviso that if there are more than 2 amino acids, they are joined together by peptide bonds in consecutive order and have a sequence identical to the sequence set forth in SEQ ID NO: 1 beginning with the I at position 9 and extending therefrom in the amino terminal direction;

wherein β represents from 0 to 13 amino acids, with the proviso that if there are more than 2 amino acids, they are joined together by peptide bonds in consecutive order and have a sequence identical to the sequence set forth in SEQ ID NO: 1 beginning with the P at position 19 and extending therefrom in the carboxy terminal direction;

wherein λ represents a carboxyl group or an amidated carboxyl group;

wherein θ represents an amino group or an acetylated amino group;

wherein all of α,Y,D,I,N,Y,Y,T,S,E and β are joined together by peptide bonds, further provided that at least two tyrosines in the compound are sulfated, wherein Δ is peptidyl or nonpeptidyl agent, and the solid line represents a peptide linker, or a peptide, disulfide, or other chemical bond.

In one embodiment, the Δ is a nonpeptidyl agent, and the nonpeptidyl agent polyethylene glycol.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

First Series of Experiments

A. Materials

Purified recombinant CD4-IgG2 protein was produced by Progenics Pharmaceuticals, Inc. from plasmids CD4-IgG2-HC-pRcCMV and CD4-kLC-pRcCMV as described (Allaway et al. AIDS Res. Hum. Retroviruses 11:533, 1995). Soluble CD4 is commercially available (NEN Life Science Products, Boston, Mass.). Anti-CCR5 MAb 2D7 was purchased from Pharmingen (San-Diego, Calif.).

The plasmids designated PPI4-tPA-gp120$_{JR-FL}$-V$^{(-)}$ and PPI4-tPA-gp120$_{DH123}$ were prepared as described (Hasel et al, U.S. Pat. Nos. 5,869,624 and 5,886,163). Monomeric gp120 glycoproteins were produced in CHO cells stably transfected with the PPI4-tPA-gp120 plasmids and purified to homogeneity as described (Hasel et al. U.S. Pat. Nos. 5,869,624 and 5,886,163; Trkola et al. Nature 384:184, 1996). The antibodies designated PA8, PA10, PA12 and PA14 were prepared by growing the corresponding hybridoma cell line in mouse ascites and isolating the antibody using protein A affinity chromatography as described (Olson et al. J. Virol. 73:4145, 1999). L1.2-CCR5$^+$ cells were cultured as described (Olson et al. J. Virol. 73:4145, 1999).

Peptides containing different segments of the CCR5 Nt were custom-synthesized by solid-phase fluorenylmethoxycarbonyl chemistry using phospho- and sulfo-tyrosine precursors as building blocks where indicated (FIG. 6). Biotinylated versions of peptides S-10/14 and P-10/14 incorporated a C-terminal GAG spacer preceding a biotinylated lysine.

Following cleavage from the resin, peptides were purified by reverse-phase chromatography on C18 columns (Vydac, Hesperia, Calif.) and analyzed by HPLC and mass spectroscopy. FIG. 6 describes the different peptides that were used in this study.

Binding of gp120 to CCR5

A gp120/CD4 complex formed from monomeric gp120 (100 nM) and biotinylated CD4-IgG2 (50 nM) was added to $1 \times 10^6$ L1.2-CCR5$^+$ cells in the presence of different concentrations of peptide (Olson et al. J. Virol. 73:4145, 1999). CD4-IgG2 is tetrameric and therefore binds four molecules of gp120, which increases binding of the complex to CCR5 (Allaway et al. AIDS Res. Hum. Retroviruses 11:533, 1995). The mean fluorescence intensity (m.f.i.) was measured by flow cytometry after addition of phycoerythrin (PE)-labeled streptavidin (Becton Dickinson, San Jose, Calif.). Inhibition of gp120/CCR5 binding was calculated: (m.f.i. with peptide)/(m.f.i. without peptide)×100%.

It was first tested whether tyrosine-sulfated peptides spanning amino acids 2–18 of the CCR5 Nt could inhibit binding of the gp120$_{JR-FL}$/CD4-IgG2 complex to CCR5$^+$ cells. The HIV-1$_{JR-FL}$ isolate exclusively uses CCR5 as a co-receptor (Dragic et al. Nature 381:667, 1996). Only peptides S-3/10/14 and S-10/14 inhibited complex binding to the cells in a dose-dependent manner (FIG. 1a). Peptides S-10 and S-14 had no inhibitory activity, even at the highest concentrations (FIG. 1a). Peptide TS-10/14, spanning amino acids 10–14, did not inhibit gp120$_{JR-FL}$/CD4-IgG2 binding to CCR5$^+$ cells, despite the presence of two sulfo-tyrosine residues (FIG. 1b).

Tyrosine-phosphorylated peptides P-10/14 and P-3/10/14 did not inhibit gp120$_{JR-FL}$/CD4-IgG2 binding to CCR5$^+$ cells (FIG. 1b). As further specificity controls we synthesized peptides containing the first seventeen residues of the CCR5 Nt in random order with sulfo-tyrosines in positions 10 and 14 (SS-10/14) or in positions 2 and 12 (SS-2/12). Neither one of these peptides reduced gp120$_{JR-FL}$/CD4-IgG2 binding to CCR5$^+$ cells, even at the highest concentrations (FIG. 1b).

Surface Plasmon Resonance Measurements (BIAcore)

Streptavidin-coated sensor chips (BIAcore AB, Sweden) were conditioned with five injections of regeneration solution (1M NaCl, 50 mM NaOH) and equilibrated with HBS-EP buffer (10 mM HEPES, 150 mM NaCl, 3M EDTA, 0.005% polysorbate 20) as recommended by the manufacturer. Biotinylated peptides were then immobilized on the chip by injection of peptide (100 nM) in HBS-EP buffer, followed by an injection of regeneration solution and equilibration with HBS-EP buffer. 400 resonance units (RU) of peptide were bound to the sensor chip surface. Solutions of the following proteins (100 nM) were passed over the sensor chip surface: gp120, sCD4, gp120/sCD4, PA8, PA10 and 2D7. Surface plasmon resonance was monitored and displayed in arbitrary resonance units (RU) as a function of time. Following injection of each solution the chip was regenerated and equilibrated as described above.

Biotinylated peptide was attached to the streptavidin-coated gold surface of a sensor chip and solutions containing different gp120/sCD4 complexes were flowed over the immobilized peptide. Adsorption of the complex due to complex/peptide binding was detected by an increase in surface plasmon resonance signal (RU), which reports changes in the effective refraction index very near the gold surface of the sensor chip (Schuck Ann. Rev. Biophys Biomol Struct 26:541, 1997). For proteins of similar size, such as the different gp120/sCD4 complexes, RU plateau values are directly proportional to the amount of protein bound to the peptide.

Specific association of the gp120$_{JR-FL}$/sCD4 complex with the sulfo-tyrosine-containing peptide bS-10/14 was accompanied by a significant increase in RU (FIG. 2a). The signal plateau but not the shape of the sensograms varied with gp120$_{JR-FL}$/sCD$^4$ concentration indicating that the peptide/complex interaction was dose-dependent (data not shown). The sensorgram obtained with bP-10/14 is similar to the one obtained in the absence of peptide, indicating a complete lack of association of the phosphorylated peptide with the protein complex (FIG. 2a). Neither gp120$_{JR-FL}$ nor sCD4 alone produced a significant increase in RU, indicating that they did not associate with the immobilized peptides. (FIGS. 2b,c). The gp120-ΔV3$_{JR-FL}$/sCD4 complex was also unable to associate with the peptides (FIG. 2d).

To further ascertain the specificity of the peptide/complex association we performed BIAcore analyses using envelope glycoproteins from HIV-1$_{DH123}$, an R5X4 isolate, and HIV-1$_{LAI}$, an X4 isolate (5). Gp120$_{DH123}$/sCD4 associated specifically with the sulfated peptide, although the plateau RU values were lower than those observed with gp120$_{JR-FL}$/sCD4 (FIG. 2e). We did not detect any binding of gp120$_{DH123}$/sCD4 to the phosphorylated peptide (FIG. 2e), nor did gp120$_{DH123}$ alone associate with the peptides (FIG. 2f). Finally, gp120$_{LAI}$ with or without sCD4 was not able to associate with either one of the peptides (FIGS. 2g,h).

These methods could be readily modified to screen for agents that bind CCR5 or that block its interaction with antibodies, gp120 or other ligands. For example, direct binding of the agents could be analyzed as described above, where the agent is substituted for the anti-CCR5 antibody or gp120/sCD4 complex. In another embodiment, the agent could be mixed or pre-incubated with the anti-CCR5 antibody (or gp120/sCD4 complex) prior to passing the mixture over biosensor chips as described above.

Binding of MAbs to CCR5

L1.2-CCR5 cells (1×10$^6$) were incubated with anti-CCR5 MAb (50 nM)±peptide (100 μM). MAb binding was detected using a PE-labeled goat anti-mouse antibody (Caltag Laboratories, Burlingam, Calif.). The m.f.i value was measured by flow cytometry as described (Olson et al. J. Virol. 73:4145, 1999). MAb binding was calculated as above.

We determined whether the CCR5 Nt peptides could inhibit binding of a panel of anti-CCR5 MAbs to CCR5$^+$ cells. PA8 binding was reduced significantly by all wild-type peptides containing amino acids 2–18, regardless of tyrosine modification (FIG. 3). BIAcore analysis confirmed that PA8 similarly and specifically associated with both sulfated and phosphorylated peptides (FIG. 4). Binding of PA12 to CCR5 was not inhibited by any of the peptides (FIG. 3). PA10 binding to CCR5 was inhibited only by S-3/10/14 (FIG. 3). PA10 was also observed to associate with bS-10/14 and to a lesser extent with bP-10/14 in BIAcore analysis (FIG. 4), which may be more sensitive than the gp120/CCR5-binding assay. Binding of 2D7 to CCR5 was not inhibited by any of the peptides (FIG. 3). No significant interaction was observed between any CCR5 Nt peptide and Mab 2D7 (FIGS. 3 and 4), whose epitope resides within the second extracellular loop on CCR5.

Single Cycle HIV-1 Entry Assay

Nlluc$^+$env$^-$ particles pseudotyped with envelope glycoproteins from MuLV, HTLV-1 and HIV-1 strains JR-FL, HxB$_2$, DH123, Gun-1 were made as described (Dragic et al. J. Virol. 72:279, 1998). Target cells (Hela-CD4$^+$CCR5$^+$ or U87-CD4$^+$CCR5$^+$) were incubated with virus-containing supernatant fractions (100 ng/ml p24)±peptide (100 μM) for 4 h. then washed and resuspended in culture media. After 48 hours the cells were lysed and luciferase activity (relative light units, r.l.u.) was measured using a standard kit (Promega, Madison, Wis.) as described (Dragic et al. J. Virol. 72:279, 1998). Viral entry was calculated: (r.l.u. with peptide)/(r.l.u without peptide)×100%.

The ability of different CCR5 Nt peptides to inhibit HIV-1 entry into CD4$^+$CCR5$^+$CXCR4$^+$ cells was tested using a luciferase-based single round of entry assay (5). Only peptides S-10/14 and S-3/10/14 inhibited the entry of the R5 isolate HIV-1$_{JR-FL}$ by approximately 50% in HeLa-CD4$^+$ CCR5$^+$ and U87MG-CD4$^+$CCR5$^+$ (FIG. 5 and data not shown). We were unable to inhibit the entry of the R5X4 isolates HIV-1$_{DH123}$ and HIV-1$_{Gun-1}$, or of the X4 isolate HIV-1$_{HxB2}$. The entry of MuLV and HTLV pseudotypes was also unaffected by the peptides (FIG. 5).

Screening Assays

1) HIV-1 gp120/CD4-I9G2

Streptavidin-coated 96-well microtiter plates (NEN Life Science Products, Boston, Mass.) are blocked with 200 μl/well of 5% bovine serum albumin (Sigma, St. Louis, Mo.) in PBS buffer and washed with assay buffer (0.5% Tween 20, 1% fetal bovine serum, and 2% BSA in PBS buffer). The plates are then incubated 1 hour at ambient temperature with 100 μl/well of biotinylated CCR5 N-terminal sulfopeptide at a concentration of 500 μM in assay buffer. Following a wash step, the plates are incubated for 1 hour at ambient temperature with an HIV-1$_{JR-FL}$ gp120/CD4-IgG2 complex in the presence or absence of inhibitory agent. The plates are again washed and incubated for 30 minutes with a horseradish peroxidase-labeled goat antibody to human IgG (Kirkegaard & Perry Laboratories, Gaithersburg, Md.) followed by addition of the TMB (3,3',5,5'-tetramethylbenzidine) chromogenic substrate (Pierce). The reaction is stopped by addition of 100 μl/well of 2N H$_2$SO$_4$ prior to calorimetric detection at a wavelength of 450 nm. Wells without biotinylated peptide serve as negative controls. The percent inhibition of binding is calculated as [1−(OD$_{with\ inhibitor}$−OD$_{control\ well}$)/(OD$_{without\ inhibitor}$−OD$_{control\ well}$)]×100, where OD represents the average optical density observed for the indicated wells.

2) Anti-CCR5 antibodies

Streptavidin-coated microtiter plates are blocked and incubated with CCR5 N-terminal peptide as described above. Following a wash step, the plates are incubated for one hour at ambient temperature with the anti-CCR5 antibody PA10 in the presence or absence of inhibitory agent. The plates are again washed and incubated for 30 minutes with a horseradish peroxidase-labeled goat antibody to mouse IgG (Kirkegaard & Perry Laboratories, Gaithersburg, Md.) followed by addition of TMB substrate for colorimetric detection as described above. The percent inhibition mediated by the inhibitory agent is calculated as described above.

Discussion

Tyrosine-modified peptides spanning the region of the CCR5 Nt that contains residues important for viral entry were synthesized. (Dragic et al. J. Virol. 72:279, 1998; Rabut et al. J. Virol. 72:3464, 1998; Farzan et al. J. Virol. 72:1160, 1998; Dorantz et al. J. Virol. 71:6305, 1997). Interactions between the Nt peptides and gp120/CD4 complexes were characterized. Peptides containing sulfo-tyrosines in positions 10 and 14 efficiently inhibited binding of $gp120_{JR-FL}$/CD4 to CCR5. Substitution of the sulfate groups for phosphates, which are also negatively charged at physiological pH, rendered the Nt peptides inactive. Inhibition of gp120/CCR5 binding was dependent, therefore, on the presence of sulfate moieties and was not simply due to non-specific electrostatic interactions between the peptide and the gp120/CD4 complex or the peptide and the cell surface. Inhibition of gp120/CCR5 binding was also dependent on the primary structure surrounding the sulfo-tyrosines since peptides with random sequences of CCR5 amino acids 2–18 had no inhibitory activity. Additional Nt amino acids in the region 2–18 were important for activity since a shortened peptide containing just amino acids 10–14 was unable to inhibit gp120/CD4 binding, despite the presence of two sulfo-tyrosines. It would be straightforward to define the minimum number of amino acids needed for activity by systematically synthesizing sulfopeptides intermediate in length between peptide 2–18 and peptide 10–14. Similarly, sulfopeptides that incorporate a greater portion of the CCR5 Nt could be easily synthesized and tested for activity using the methods described herein.

Qualitative BIAcore analyses allowed the demonstration of a highly specific, CD4-dependent interaction between a tyrosine-sulfated Nt peptide and $gp120_{JR-FL}$. No binding of the protein complex to a tyrosine-phosphorylated peptide was observed. Only gp120s derived from isolates that use CCR5 as a co-receptor associated with the sulfated peptide. $Gp120_{DH123}$/CD4 binding was weaker than $gp120_{JR-FL}$/CD4 binding, suggesting that envelope glycoproteins from R5X4 isolates have a lower apparent affinity for CCR5 than envelope glycoproteins from R5 isolates $gp120_{LAI}$, derived from an isolate that only uses CXCR4, did not bind to the sulfated peptide. A V3 loop-deleted $gp120_{JR-FL}$ did not associate with the sulfated peptide, just as this protein was unable to bind to full length CCR5 on the cell surface (Trkola et al. Nature 384:184, 1996).

The binding of the Nt peptides to several anti-CCR5 MAbs, all of which recognize conformational epitopes in CCR5 and inhibit gp120/CCR5 binding were also studied. PA12 and 2D7 did not bind to any of the peptides. Binding of PA8 to the peptides was independent of tyrosine-modification whereas PA10 associated more with the sulfo-tyrosine-containing peptide than with the phospho-tyrosine-containing peptide. It seems, therefore, that sulfo-tyrosines and phospho-tyrosines are relatively interchangeable for the purpose of MAb binding but that gp120/CD4 binding has an absolute requirement for sulfo-tyrosines. Relatively subtle differences in size and geometry of sulfate and phosphate groups might be relevant for binding of the CCR5 Nt with gp120, which must not only accept the negative charge, but also coordinate, probably by hydrogen bonds, the tyrosine sulfate oxygens. The kinetics of MAb binding to the CCR5 Nt peptides exhibited large apparent on rates and slow apparent off rates, which also differed from our observations of gp120/CD4 binding kinetics.

None of the Nt peptides inhibited MuLV, HTLV and $HIV-1_{HxB2}$ envelope-mediated viral entry, which is not mediated by CCR5. In contrast, peptides S-10/14 and S-3/10/14 specifically inhibited the entry of the $HIV-1_{JR-FL}$ R5 strain in two different cell lines. The inhibition of HIV-1 entry by tyrosine-sulfated peptides was partial (~50%) but nonetheless striking given the difficulty of blocking this process with short, linear peptides (Jameson et al. Science 240:1335, 1988; Chan and Kim Cell 93:681:1998; Doranz et al. J. Exp. Med. 186:1395, 1997; Heveker et al. Current Biology 8:369, 1998; Eckert et al. Cell 99:1, 1999).

References for First Series of Experiments

1. E. A. Berger et al. (1999) Annu Rev Immunol 17: 657–700.
2. A. Trkola et al. (1996) Nature 384: 184–187.
3. L. Wu et al. (1996) Nature 384: 179–183.
4. Y. J. Zhang et al. (1999) J. Virol 73: 3443–3448.
5. T. Dragic et al. (1998) J. Virol. 72: 279–285.
6. G. E. Rabut et al. (1998) J. Virol. 72:3464–3468.
7. M. Farzan et al. (1998) J. Virol. 72:1160–1164.
8. B. J. Doranz et al. (1997) J. Virol. 71: 6305–6314.
9. M. Farzan et al. (1999) Cell 96:667–676.
10. P. A. Baeuerle et al. (1987) J. Cell Biol 105:2655–2664.
11. J. W. Kehoe et al. (2000) Chemistry & Biology 7:R57–R61.
12. M. Baba et al. (1988) Proc Natl Acad Sci USA 85: 6132–6136.
13. D. Schols et al. (1990) Virology 175: 556–561.
14. G. Roderiquez (1995) J. Virol 69: 2233–2239.
15. S. S. Hwang et al. (1991) Science 253: 71–74.
16. F. Safaiyan et al. (1999) J. Biol Chem 274: 36267–36273.
17. P. A. Baeuerle et al. (1986) Biochem Biophys Res Commun 141: 870–877.
18. W. C. Olson et al. (1999) J Virol 73:4145–4155.
19. G. P. Allaway et al. (1995) AIDs Res Hum Retroviruses 11: 533–539.
20. T. Dragic et al. (1996) Nature 381:667–673.
21. P. Schuck et al. (1997) Annu Rev Biophys Biomol Struct 26:541–566.
22. S. Lederman et al. (1989) J. Immunol 143:1149–1154.
23. S. Ohlson et al. (2000) Trends in Biotechnology 18: 49–52.
24. B. A. Jameson et al. (1988) Science 240: 1335–1339.
25. D. C. Chan et al. (1998) Cell 93: 681–684.
26. B. J. Doranz et al. (1997) J. Exp Med 186: 1395–1400.
27. N. Heveker et al. (1998) Current Biology 8:369–376.
28. D. M. Eckert et al. (1999) Cell 99: 1–20.
29. H. Sakaida et al. (1998) J. Virol 72: 9763–9770.
30. S. E. Kuhman et al. (1997) J. Virol 71: 8642–8656.
31. T. M. Ross et al. (1998) J. Virol 72: 1918–1924.
32. R. E. Atchison et al. (1996) Science 274: 1924–1926.
33. P. D. Bieniasz et al. (1997) EMBO 16: 2599–2609.
34. A. L. Edinger et al. (1999) J. Virol 73:4062–4073.
35. J. Rucker et al. (1996) Cell 87: 437–446.
36. L. Picard et al. (1997) J. Virol 71: 5003–5011.
37. T. Dragic et al. (2000) Proc Natl Acad Sci 10: 1073.
38. P. D. Kwong et al. (1998) Nature 393: 648–659.
39. C. D. Rizzuto et al. (1998) Science 280: 1949–1953.

40. P. D. Kwong et al. (2000) J. Virol 74: 1961–1972.
41. M. Moulard et al. (2000) J. Virol 74: 1948–1960.
42. A. Trkola et al. (1996) Nature 384: 184–186.
43. B. Labrosse et al. (1998) J. Virol 72: 6381–6388.
44. Spetzler et al. (1995) J. Pept. Prot Res 45: 78.
45. Yai et al. Et al. (1995) J. Virol 69: 320.
46. Okuda et al. (1993) J. Mol. Recognit. 6:101.
47. Sabatier et al. (1993) Biochemistry 32: 2763.
48. Frank et al (2000) Journal of Biological Chemistry 275. No. 16: 11672–11677.
49. C. Cohen et al (1990) Proteins 7:1–15.
50. A. Lupas (1996) Trends Biochem Sci 21:375–382.
51. R. A. Kammerer (1996) Matrix Biol 15: 555–565.
52. W. D. Kohn (1997) J. Biol. Chem. 272:2583–2586.
53. C. Wild (1993) AIDS Res Hum Retroviruses, 9:1051–1053.
54. C Wild (1994) Proc Natl Acad Sci U S A; 91:9770–9774.
55. U.S. Pat. No. 4,816,567, issued Mar. 28, 1989 to Cabilly et al.
56. U.S. Pat. No. 5,225,539, issued Jul. 6, 1993 to Gregory Winter.
57. U.S. Pat. No. 5,585,089, issued Dec. 17, 1996 to Queen et al.
58. U.S. Pat. No. 5,693,761, issued Dec. 2, 1997 to Queen et al.
59. PCT International Application No. PCT/US89/05857, filed Dec. 28, 1989, published Jul. 26, 1990, WO 90/07861.
60. Clercq, E. D. et al. (1994) *Antimicrobial Agents and Chemotherapy* 38:668–674.
61. Clercq, E. D. et al (1992) *Proc. Natl. Acad. Sci. USA* 89: 5286–5290.
62. Merrifield, R. B. (1963) *J. Am. Chem. Soc.* 85: 2149–2154.
63. Goeghegan, K. F. Stroh, J. F. (1992) *Bioconjugate Chem.* 3: 138–146.
64. Baba, M. et al. (1999) Proc. Natl Acad Sci USA, 96(10):5698–5703.
65. Schols D. et al (1997) Antiviral Res, 35(3):147–156.

Second Series of Experiments

CD4 and CCR5 mediate fusion and entry of R5 HIV-1 strains. Sulfotyrosine and other negatively charged residues in the CCR5 amino-terminal domain (Nt) are crucial for gp120 binding and viral entry. It is shown that a soluble gp120/CD4 complex specifically binds to a peptide corresponding to CCR5 Nt residues 2–18, with sulfotyrosines in positions 10 and 14. This sulfopeptide also inhibits soluble gp120/CD4 binding to cell surface CCR5 as well as infection by R5 virus. These observations prompted the further delineation of the determinants of the gp120-CCR5 Nt sulfopeptide interaction. It is shown that residues 10–18 constitute the minimal domain of the CCR5 Nt that is able to specifically interact with soluble g120/CD4 complexes. In addition to sulfotyrosines in positions 10 and 14, negatively charged residues in positions 11 and 18 participate in this interaction. Furthermore, the CCR5 Nt binds to a CD4-induced surface on gp120 that is composed of conserved residues in the V3 loop stem and the C4 domain. Binding of gp120 to cell surface CCR5, however, is further influenced by variable residues in the crown of the V3 loop. This data suggest that gp120 docking to CCR5 is an interdependent, multi-step process involving different regions of the envelope glycoprotein and the co-receptor.

Entry of HIV-1 R5 isolates into target cells is mediated by the successive interaction-of the envelope glycoprotein gp120 with CD4 and the CCR5 co-receptor [3]. Gp120-CD4 complex formation generates a large bonding energy that drives reordering of the gp120 core structure [22, 31, 47]. Changes in the orientation of the V1/V2 and V3 loops, as well as the bridging sheet (composed of the V1/V2 stem and C4), cooperatively create and/or expose a co-receptor binding site on gp120 [22,37,47]. The predicted co-receptor binding surface on gp120 has a hydrophobic core surrounded by a positively charged periphery and is composed of both conserved and variable residues located in the C4 domain and V3 loop, with lesser contributions from the V1V2 stem [22, 36, 37].

It has been demonstrated that specific amino acids within the CCR5 amino-terminal domain (Nt, amino acids 2–31), including negatively charged and tyrosine residues, are essential for CCR5-mediated fusion and entry of R5 and R5X4 HIV-1 strains [5, 12, 13, 15, 35]. Farzan et al. [16] demonstrated that the CCR5 Nt undergoes both O-glycosylation and tyrosine sulfation. It is presently not known whether O-glycosylation plays a role in co-receptor function, but this possibility is suggested by observations that serines in the Nt are important for viral entry. Inhibition of cellular sulfation pathways, including tyrosine sulfation, greatly decreases gp120 binding to CCR5 as well as the entry of R5 and R5X4 HIV-1 strains into target cells ([16], E.G.C. unpublished data) Post-translational sulfation of the tyrosine residues in the CCR5 Nt, therefore, may critically modulate the susceptibility of target cells to HIV-1 infection in vivo.

It was demonstrated that a CCR5 Nt-based peptide spanning residues 2–18 and containing sulfotyrosines in positions 10 and 14 specifically associates with soluble gp120/CD4 complexes containing envelope glycoproteins from R5 (JR-FL) and R5X4 (DH123) but not X4 (LAI) strains [11] Peptides containing unmodified tyrosines or phosphotyrosines, however, did not bind soluble gp120/CD4 complexes [11]. The tyrosine-sulfated CCR5 Nt therefore specifically interacts only with gp120 proteins from isolates that use this co-receptor to gain entry into target cells. Furthermore, only the CCR5 Nt-based sulfopeptide inhibits binding of soluble gp120$_{JR-FL}$/CD4 to intact, cell surface-expressed CCR5 and moderately blocks the entry of the R5 isolate JR-FL. The affinity of soluble gp120/CD4 for the CCR5 Nt sulfopeptide, however, is approximately 10–100-fold lower than for the native, membrane-associated co-receptor [11, 42, 46], suggesting that other gp120-CCR5 contacts are required to consolidate this interaction. This concept is further supported by studies of CCR5 chimera, as well as studies with inhibitors of CCR5 co-receptor function [12, 34, 38, 32, 14].

A novel ELISA is reported to detect binding of sulfopeptides to soluble gp120/CD4 complexes, as well as anti-CCR5 MAbs and chemokines. ELISA and surface plasmon resonance (SPR) were used to further delineate the determinants of the gp120-CCR5 Nt interaction. In order to define the minimal domain of the CCR5 Nt capable of specifically binding to soluble gp120/CD4 complexes, sulfopeptides corresponding to different regions of the Nt were analyzed. To identify the gp120 domains involved in sulfopeptide binding, inhibition of gp120/CD4 complex binding to CCR5 Nt sulfopeptides by anti-gp120 Mabs was studied. Residues in or near the epitopes of inhibitory MAbs were mutated to alanine, and the gp120 point mutants were compared for their ability to bind to CCR5 Nt sulfopeptides and cell-surface CCR5. The data suggest that a mostly conserved surface of gp120 binds to a nine-residue stretch of the CCR5 Nt, whereas more variable residues in the crown of the V3 loop may interact with a secondary binding site on CCR5.

Materials and Methods

Reagents:

CD4-IgG$_2$, soluble CD4 (sCD4), recombinant soluble gp120s from HIV-1$_{LAI}$ (X4), HIV-1$_{DH123}$ (R5X4), and HIV-1$_{JR-FL}$ (R5) isolates, anti-gp120 MAb PA1 (directed against the V3 loop of JR-FL) and anti-CCR5 MAbs PA8, PA10, PA11, PA12, PA14 were produced by Progenics Pharmaceuticals, Inc. (Tarrytown, N.Y.) as described [1, 32]. MAbs 133–290, 133–192, 135–9, A32, 17b, 19b, 48d, 9284, G3–42, C11, G45–60 and 2G12 were a generous gift [26]. The small-molecule CCR5 antagonist TAK-779 was obtained as described [14].

Peptides corresponding to different segments of the CCR5 Nt were synthesized as described previously (Table 1) [11]. Sulfo- or phospho-tyrosines were incorporated in positions 10 and 14, and all peptides carried a carboxy-terminal Gly-Ala-Gly spacer preceding a biotinylated lysine. Residues were numbered according to their positions in the full length CCR5 protein.

Surface Plasmon Resonance:

Binding of gp120/CD4-IgG$_2$ complex and MAbs to CCR5 Nt-based peptides was measured as previously described [11]. Briefly, streptavidin-coated sensor chips were divided into two surfaces, each with a separate flow chamber. The sensor chip was conditioned and equilibrated as recommended by the manufacturer. Biotinylated peptide (400 resonance units, RU) was bound to the surface of the second chamber whereas the first chamber of the chip was used as a negative control. Gp120/CD4-IgG$_2$ complex (50 nM) was passed over the chip surface in the presence or absence of MAbs (150 mM). Surface plasmon resonance was monitored and displayed in RU as a function of time using a Biacore X. After each measurement the chip was regenerated and equilibrated as recommended by the manufacturer.

Generation of gp120 alanine mutants and their binding to CD4-IgG$_2$:

Mutant gp120 proteins were generated using the Quick-Change Kit from Stratagene (San-Diego, Calif.). Gp120$_{JR-FL}$, cloned into the pPPI4 expression vector [4], served as the template for site directed mutagenesis. Nucleotide sequencing was performed to ascertain the presence of the appropriate mutation in the gp120 coding sequence. 293T cells were calcium phosphate transfected with the different mutant gp120 expression constructs. Supernatants containing soluble gp120 proteins were harvested and cleared of debris by centrifugation 24 hours post-transfection. Quantification of gp120 was performed by ELISA as previously described [40]). Briefly, 293T supernatants were boiled for 5 minutes and denatured gp120 was captured on an ELISA plate coated with D7324 (International Enzymes Inc. Fallbrook, Calif.), a MAb that recognizes a 15 residue linear epitope in the carboxy-terminal end of gp120. Captured gp120 was detected by a mixture of anti-gp120 MAbs B12 and B13 [40], followed by incubation with a horseradish peroxidase-conjugated (HRP) anti-mouse IgG antibody (Amersham Pharmacia, Piscataway, N.J.). Optical density (O.D.) was measured at 450 nm using the ImmunoPure TMB Substrate kit (Pierce, Rockford, Ill.).

CD4-IgG$_2$ binding to non-denatured mutant gp120 proteins also was measured. Plates coated with D7324 were used to capture native gp120 from supernatants of transiently transfected 293T cells. CD4-IgG$_2$ (50 nM) was added to the plates and its binding was detected using an HRP-conjugated goat anti-human IgG and TMB substrate as described above.

CCR5 Nt peptide ELISAs:

Streptavidin-coated ELISA plates (Pierce, Rockford, Ill.) were blocked with D-PBS/5% BSA for 2 hours at room temperature then washed three times with assay buffer (D-PBS/0.5% Tween 20/1% Fetal Bovine Serum/2% BSA). Plates were then contacted with sulfo- or phospho-peptides (1 µg/ml) for 1 hour at room temperature and washed three times with assay buffer. Mixtures of CD4-IgG$_2$ (50 nM) and purified gp120 or gp120-containing supernatants in a 1:4 molar ratio were added to the plates for 1 hour at room temperature. Plates were washed three times and (HRP)-conjugated goat anti-human IgG was used to detect the presence of bound CD4-IgG$_2$. The plates were developed using the TMB substrate as described above. Gp120/CD4-IgG$_2$ binding to the peptides was normalized for CD4-IgG$_2$ binding to the mutant gp120 proteins.

In a competition ELISA, peptides were captured onto the plates as described above. Inhibitor or assay buffer was added for 1 h prior to addition of gp120$_{JR-FL}$/CD4-IgG$_2$ complex (1 nM) for an additional h at room temperature. The assay was then completed as described above. Direct binding of anti-CCR5 murine MAbs to the peptides was examined as described above except that MAb was substituted for gp120/CD4-IgG$_2$ complex and a goat anti-mouse HRP-coupled antibody was used for detection.

Binding of gp120/CD4-IgG$_2$ complexes to cell-surface CCR5:

L1.2-CCR5$^+$ cells ($10^6$) were incubated with gp120-containing supernatant (100 nM) and biotinylated CD4-IgG$_2$ (50 nM) for 1 hour at 37° C. in assay buffer, as previously described [32]. Gp120/CD4-IgG$_2$ bound to the cells was revealed by FACS analysis of the mean fluorescence of intensity (m.f.i.) after addition of streptavidin-PE (Pharmingen, San-Diego, Calif.). Binding was calculated using the formula: (m.f.i. Gp120 mutants)/(m.f.i. gp120 wild type)×100% and normalized for CD4-IgG$_2$ binding to the mutant gp120 proteins.

Results

An ELISA to detect binding of soluble gp120/CD4 complexes to CCR5 Nt-based peptides:

Surface plasmon resonance (SPR) was previously used to show that gp120/sCD4 complexes specifically interact with a peptide spanning CCR5 residues 2–18 and containing sulfotyrosines in positions 10 and 14 (2–18, Table 1). The on and off rates of complex-peptide binding were extremely rapid and could not be measured precisely by SPR. The Kd was estimated to be in the $10^{-7}$–$10^{-8}$ range. Replacing monomeric sCD4 with tetravalent CD4-IgG$_2$, however, lead to a dramatic shift in both on and off rates, lowering the Kd into the $10^{-8}$–$10^{-9}$ range (FIG. 7a). This observation prompted us to develop an ELISA to directly detect complex-peptide binding. Streptavidin-coated ELISA plates were used to capture biotinylated, CCR5 Nt-based peptides, and then further incubated with soluble gp120/CD4-IgG$_2$ complexes. Complex binding was detected using an HRP-conjugated goat anti-human IgG antibody.

Sulfopeptide 2–18 bound gp120$_{JR-FL}$/CD4-IgG$_2$ with an IC$_{50}$ ~1 nM, and gp120$_{DH123}$/CD4-IgG$_2$ with an IC$_{50}$ ~5 nM (FIG. 7b). Sulfopeptide 2–18 did not measurably bind CD4-IgG$_2$ alone or in complex with either gp120$_{LAI}$ or V3 loop-deleted gp120$_{JR-FL}$ (FIG. 7b and data not shown). No binding was observed to an analogous CCR5 Nt phosphopeptide (2–18(P), FIG. 12) by any of the gp120/CD4-IgG$_2$ complexes (FIG. 7b). Identical patterns of reactivity were observed for gp120s in complex with CD4-γ2, a divalent CD4-immunoglobulin fusion protein [data not shown, (1)] However, no binding was observed for gp120 in complex with anti-gp120 MAbs 2G12 and IgG1b12, even though the latter's epitope overlaps the CD4 binding site on gp120 (data not shown). Thus the ELISA reproduces the critical biological features of cell-surface CCR5/gp120 interactions, including a dependence upon CCR5 tyrosine sulfation, CD4, the V3 loop, and the coreceptor usage patterns of the parent viruses.

Using a competition ELISA, inhibition of gp120$_{JR-FL}$/CD4-IgG2 binding to the sulfopeptide 2–18 was enabled with the anti-CCR5 MAb PA8. However, binding of soluble gp120/CD4-IgG$_2$ complexes to the sulfopeptide was not inhibited by TAK-779, nor the CC-chemokines MIP-1α, MIP-1β and RANTES even when used at supraphysiologic concentrations.

Binding of CCR5 Nt peptides to anti-CCR5 MAbs and soluble gp120/CD4: ELISA was used to test the binding of a panel of anti-CCR5 MAbs to peptides 2–18 and 2–18(P). We had previously demonstrated that MAbs PA8, PA11 and PA12 bind epitopes in the Nt, PA10 binds an epitope that spans the Nt and ECL2 and PA14 binds an epitope exclusively in ECL2 [32]. Here we show that PA8 avidly binds peptides 2–18 and 2–18(P) (FIG. 2). PA10 binds avidly to 2–18 and moderately to 2–18(P). PA11 binds moderately to 2–18 and weakly to 2–18(P). PA12's binding is weak for 2–18 and undetectable for 2–18(P). Finally, PA14 does not recognize either the sulfopeptide or the phosphopeptide (FIG. 8). Furthermore, PA8 binds similarly to all of the CCR5 Nt-based sulfopeptides in FIG. 12 (data not shown).

In order to more precisely delineate the minimal CCR5 Nt domain that specifically binds to soluble gp120/CD4 complexes, a panel of sulfopeptides spanning different stretches of the CCR5 Nt were synthesized (FIG. 12). All of the peptides carried sulfotyrosines in positions 10 and 14 since we previously showed that these are required for complex-peptide binding. Binding of gp120$_{JR-FL}$/CD4-IgG$_2$ to the different sulfopeptides was tested by ELISA. Although the strongest binding was observed using longest sulfopeptide, 2–18, significant binding for peptide 10–18, which demonstrated ~3-fold lower avidity was also observed (FIG. 9). Peptides 8–15, 6–16 and 10–15 bound the soluble complex at least ten-fold less avidly than 2–18. (It was previously shown that a sulfopeptide consisting of residues 10–14 did not bind soluble gp120/CD4 complexes.) Furthermore, the gp120$_{JR-FL}$/CD4-IgG2 complex only weakly bound to peptide 10–18 carrying two alanine mutations in positions 11 and 18. Previous mutagenesis studies have shown that residues Asp-11 and Glu-18 are important for fusion, entry and gp120-CCR5 binding [12, 13]. Finally, it should be noted that the same binding patterns to the different sulfopeptides were observed with soluble complexes containing gp120$_{DH123}$ (data not shown).

Inhibition of gp120/CD4 binding to CCR5 Nt sulfopeptides by anti-gp120 MAbs:

In order to determine which domains of gp120 were involved in binding to CCR5 Nt-based sulfopeptides, the ability of a panel of well-characterized anti-gp120 MAbs [25] to inhibit binding of either the gp120$_{JR-FL}$/CD4-IgG2 or the gp120$_{DH123}$/CD4-IgG2 complex to the 2–18 sulfopeptide was tested. Only MAbs directed against CD4-induced (CD4I) epitopes and the. V3 loop were capable of inhibiting binding of the gp120/CD4-IgG2 complex to the CCR5 sulfopeptide. Inhibition of gp120$_{JR-FL}$ and gp120$_{DH123}$ binding by MAbs 17b and 48d was >90%. The anti-V3 loop MAb 19b [28], which recognizes an epitope in the crown of the V3 loop (sequence -I----G--FY-T) and is reactive with R5 strains, inhibited gp120$_{JR-FL}$ binding >90% and gp120$_{DH123}$ binding by approximately 80%. Anti-V3 loop MAb PA1, which was raised against gp120$_{JR-FL}$ (W.C.O., unpublished results) efficiently inhibited binding of gp120$_{JR-FL}$ but not gp120$_{DH123}$. Finally, anti-V3 loop MAb 9284 [21], which recognizes an epitope spanning residue 307 to 330 in the V3 loop of X4 strains, was unable to inhibit binding of either gp120 protein to the sulfopeptide. MAbs directed against other epitopes in other constant and variable regions of gp120 also had no effect on binding of the soluble complex to the peptides. Similar results were obtained when the anti-gp120 MAbs were used to inhibit soluble complex binding to cell surface CCR5 (data not shown).

Binding of mutant soluble gp120/CD4 complexes to CCR5 Nt sulfopeptides:

Numerous studies have shown that residues in the V3 loop determine co-receptor usage and binding [6–10, 18, 20–21, 23–24, 27, 29, 33, 41–44, 46]. The crystal structure of a gp120 lacking the V1/V2 and V3 loops in complex with sCD4 and the 17b MAb further implicated a conserved, CD4i surface on gp120, adjacent to the V3 loop, in co-receptor binding [36, 37]. Single alanine mutants of all of the residues near or within regions previously shown to be important for co-receptor usage were generated. These gp120 mutants were tested for their ability to bind to the CCR5-based sulfopeptide 2–18 as well as to cell surface CCR5. Binding was normalized for gp120 mutant binding to CD4-IgG$_2$. Wild-type levels of binding were observed for all mutants except W427A, R440A and R469A, which bound CD4-IgG$_2$ with, 5–10-fold lower but nonetheless measurable avidity.

Residues in both strands of the V3 loop stem were found to be involved in gp120 binding to the 2–18 sulfopeptide: Alanine mutants of residues R298, N301, T303, I322, D324, I325 and R326 were found to decrease complex binding to the peptide by >10-fold. Residues in the crown of the V3 loop, including the GPGR motif, however, had no effect on gp120 binding to the sulfopeptide. C4 residues in or adjacent to the two C-terminal β-strands of the bridging sheet were also shown to participate in binding to the sulfopeptide: Alanine substitutions of R419, I420, K421, Q422 and R444 decreased complex binding to the sulfopeptide by 5–10-fold. None of the alanine substitutions that we introduced in the other regions of gp120 significantly affected complex-peptide-interactions.

It was furthermore demonstrated that additional gp120 residues are involved in complex binding to cell surface expressed CCR5. Alanine substitutions of residues S306, G310, P311, R313, F315, Y316 in the crown of the V3 loop decreased complex binding to CCR5 by 5–10-fold.

Furthermore, alanine substitutions of several residues in C1, C2 and C3 also had a moderate effect on complex binding to CCR5. Finally, it is noted that alanine substitutions of R440 and R469 increased complex binding to both 2–18 and CCR5, whereas substitutions of E320 and W427 increased complex binding to CCR5 only.

Discussion

Tyrosine-sulfated CCR5 Nt peptides were studied for binding to soluble gp120/CD4 complexes as well as anti-CCR5 MAbs, CC-chemokines and TAK-779 using a novel solid-phase ELISA. Inhibition of peptide-complex interactions by anti-gp120 MAbs was explored by surface plasmon resonance. These Mabs were also tested for their ability to inhibit complex binding to cell surface CCR5. In addition, a panel of gp120 point mutants were generated and then their reactivity was compared with CCR5 Nt peptides and cell surface CCR5. The principal conclusions are that (1) residues 10 to 18 of the CCR5 Nt may define the minimum recognition site for gp120, (2) gp120 binding to the CCR5 Nt depends on highly conserved residues located in the C4 domain and the stem of the V3 loop, and (3) gp120 binding to cell surface CCR5 depends on a broader region that includes residues in the crown of the V3 loop, C1, C2 and C3. The findings suggest that distinct domains of gp120 and CCR5 bind in a multi-step fashion and raise questions about the determinants of specificity of the co-receptor-gp120 interaction.

An ELISA was developed to detect complex-peptide binding based on the observation that the tetravalent gp120/CD4-IgG$_2$ complex binds to CCR5 Nt sulfopeptides ten-to a hundred-fold more avidly than the monovalent gp120/sCD4 complex. Complex-sulfopeptide binding was only observed with gp120 proteins derived from R5 and R5X4, but not X4 HIV-1 strains. V3 loop deleted gp120$_{JR-FL}$ failed to bind to the sulfopeptides. Phosphopeptides did not bind to any of the soluble complexes. Thus, the ELISA reproduces the critical biological features of cell-surface CCR5-gp120 interactions, including a dependence upon CD4, CCR5 tyrosine sulfation, the V3 loop and the co-receptor usage patterns of the parental viruses.

CCR5 Nt phosphopeptides and sulfopeptides were differentially recognized by anti-CCR5 MAbs in ELISA. PA8 possessed equal avidity for sulfated and phosphorylated peptides, implying that its epitope does not include tyrosine side chains. PA10 and PA11 preferentially recognized the sulfopeptide, albeit with varying efficiencies, suggesting that sulfotyrosines participate either directly in peptide-MAb interactions or indirectly by influencing epitope conformations. PA12 only interacted with the sulfopeptide and PA14 did not bind either Nt peptide. It was previously shown that both of these MAbs recognize discontinuous epitopes comprising residues in the Nt and ECL2 of CCR5. The observations now imply that ECL2 residues are marginal for PA12 binding and essential for PA14 binding to CCR5. Finally, binding of soluble gp120/CD4 complexes to CCR5 Nt peptides could be completed with an anti-CCR5 Mab but not with either CC-Chemokines or TAK-779, whose binding sites have been mapped to other regions of CCR5 (14, 39). Both CC-chemokines and TAK-779, however, are able to compete with gp120/CD4 binding to cell surface CCR5, perhaps through steric or conformational mechanisms. (14, 42, 46). It is noted that Farzan et al. reported that a CCR5 Nt sulfopeptide spanning residues 1–22 partially blocks MIP-1α binding to cell-surface CCR5 and we attribute the discrepancy to differences in peptides and assays (17).

In order to more precisely delineate the gp120 binding site in the CCR5 Nt, an ELISA was used to test binding of soluble complexes to several CCR5 Nt sulfopeptides. 10–18 was the smallest sulfopeptide that avidly bound soluble gp120/CD4 complexes and may define the minimum docking site for gp120 on CCR5. In addition to the two sulfotyrosines in positions 10 and 14, negatively charged amino acids D11 and E18 were found to be critical for complex-peptide binding. It was concluded that a cluster of negative charges in the CCR5 Nt appears to represent the principal recognition motif for gp120, although residues 2 to 9 further contribute to binding. Similar patterns of peptide reactivity were observed for recombinant gp120s derived from HIV-1$_{JR-FL}$ (R5) and HIV-1$_{DH123}$ (R5X4), suggesting that the CCR5 Nt sulfopeptides recognize conserved structures in the envelope glycoprotein. Gp120$_{DH123}$, however, bound about five-fold less that gp120$_{JR-FL}$ to the sulfopeptides, which probably accounts for its less efficient usage of CCR5 (13).

Anti-gp120 MAbs were tested for their ability to inhibit gp120/CD4 binding to sulfopeptides or to cell surface CCR5. A number of anti-gp120 MAbs directed against conserved and variable regions of the envelope glycoprotein were not inhibitory. Only Mabs 48d and 17b, directed against CD4i epitopes, and 19b and PA1, directed against the V3 loop, efficiently inhibited gp120 binding to the 2–18 sulfopeptide and to cell surface CCR5. The CD4i epitope was previously shown to participate in co-receptor binding and residues in the V3 loop primarily determine co-receptor specificity (36, 37). The results now suggest that these regions of gp120 determine its association with the CCR5 Nt. It is noted that inhibition of peptide-complex binding by 19b, which recognizes an epitope in the V3 crown, is inconsistent with the finding by gp120 mutagenesis experiments that residues in the V3 loop crown do not participate in complex-peptide binding. This leads to a conclusion that the inhibitory effect of 19b may be steric hindrance.

In order to determine more precisely the regions of gp120 that modulate the gp120-CCR5 interaction, the binding of a panel of gp120 point mutants to the CCR5 Nt sulfopeptide and to cell surface CCR5 was tested. The mutants were created by the introduction of single alanine substitutions near or within regions previously shown to be important for the integrity of the CD4i epitope and/or CCR5 binding (36, 37). Highly conserved residues in C4 and the V3 loop stem, including for arginines and a lysine, were found to affect binding of gp120 to the CCR5 Nt sulfopeptide (FIG. 13). These residues are located in two random coil segments of C4 that straddle the V3 loop stem and may constitute a positively charged CCR5 Nt binding domain (22). Additional, conserved residues in the crown of the V3 loop, C1, C2 and C3 contribute to gp120 binding to cell surface CCR5 (FIG. 13). It remains to be determined whether these residues interact with other extracellular domains of CCR5 or whether they influence the conformation of C4 and the V3 loop stem in a way that is only relevant in the context of gp120/CD4 binding to cell surface CCR5. It is unlikely that these residues also interact with the Nt in the context of cell surface CCR5 because they are relatively distal from the C4 and V3 residues that were implicated in sulfopeptide binding (22).

To date, several lines of evidence suggest that gp120 binds to more that one region of the CCR5 co-receptor: (1) the affinity of gp120s/CD4 for the CCR5 Nt sulfopeptide is approximately 10–100-fold lower that for the native, membrane-associated co-receptor (11, 42, 46), (2) co-receptor chimera studies implicate the extracellular loops in viral fusion and entry (2, 12, 34, 38) and (3) inhibitors of CCR5 co-receptor function such as Mabs 2D7 and PA14, as well as TAK-779 do not bind to the CCR5 Nt yet block gp120/CD4 binding to CCR5 (14, 32). The present findings could be interpreted to support a distributed model for gp120-CCR5 interactions that mirrors the two-site paradigm proposed for the interaction of certain chemokines with their receptors (30, 45). In this model, binding is initially driven by electrostatic interactions between negatively charged residues in the receptor Nt and basic surfaces on the chemokine ligand. This binding serves to orient the ligand and promote its interactions with other portions of the chemokine receptor. The V3 loop crown may form initial electrostatic interactions with the extracellular loops of CCR5, which would allow the CCR5 Nt to bind to a conserved region of gp120 comprising residues in C4 and the V3 loop stem.

Alternatively, the CCR5 Nt could first bind the C4/V3 stem domain, which would them promote an interaction of the V3 loop with some other region of CCR5. All of these interactions involve additional gp120 residues that we have yet to identify. The role of the putative second interaction is unclear but it may further stabilize the gp120-CCR5 interaction, optimally orienting the fusion apparatus, or triggering gp41 conformational changes that are required for fusion.

The findings present us with a seeming paradox wherein nine residues of the CCR5 Nt confer specificity on the CCR5-gp120 interaction by binding to gp120 residues that are highly conserved among clade B isolates, regardless of their co-receptor usage. However, although the C4 and V3 stem residues themselves are conserved, their precise placement may differ for R5 and X4 viruses. Clearly, relatively minor differences in the orientation, exposure or relative positioning of these widely separated residues could abrogate binding to a short peptide but not a MAb (e.g., 17b) possessing a larger, more distributed binding site (37). In addition, more variable amino acids (e.g., 324) within or outside the C4/V3 loop stem may contribute to the specificity of the gp120-Nt interaction, and we showed that residues N279, R313, P369 and R444 participate in gp120/CD4 binding to cell surface CCR5 but not to CCR5 Nt sulfopeptides. Future studies employing additional gp120 mutants together with CCR5 mutants and CXCR4-based sulfopeptides will shed light on the specificity determinants of the gp120-co-receptor interaction. CD4 and CCR5 mediate fusion and entry of R5 HIV-1 strains. Sulfotyrosines and negatively charged residues in the CCR5 Nt are crucial for binding of gp120 and viral entry. Soluble gp120/CD4 complexes specifically bind to CCR5 Nt peptides containing sulfotyrosines in positions 10 and 14. CCR5 Nt sulfotyrosines inhibit gp120/CD4 binding to CCR5 as well as viral entry. Residues in the V3 loop and the C4 region of gp120 compose a binding site for the CCR5 amino terminal domain. Residues 10–18 of the CCR5 Nt constitute a minimal binding domain for gp120: sulfotyrosines Y10 and Y14 and negatively charged residues D11 and E18 are important for binding. The CCR5 Nt terminal binding site on gp120 is composed mostly of residues in the V3 loop stem and the C4 domain.

References for the Second Series of Experiments

1. Allaway, G P., 1995. Expression and characterization of CD4-IgG2, a novel heterotetramer that neutralizes primary HIV type 1 isolates. Aids Res Hum Retroviruses. 11:533–539.
2. Atchison, R. E., 1996. Multiple extracellular elements CCR5 and HIV-1 entry: dissociation from response to chemokines. Science. 274:1924–1926.
3. Berger, E. A., 1999. Chemokine receptors as HIV-1 coreceptors: roles in viral entry, tropism, and disease. Annu Rev Immunol. 17:657–700.
4. Binley, J. M., 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol. 74:627–643.
5. Blanpain, C., 1999. Multiple charged and aromatic residues in CCR5 amino-terminal domain are involved in high affinity binding of both chemokines and HIV-1 env protein. J. Biol. Chem. 274:34719–34727.
6. Chan, S. Y., 1999. V3 recombinants indicate a central role for CCR5 as a coreceptor in tissue infection by human immunodeficiency virus type 1. J Virol. 73:2350–2358.
7. Chavda, S. C., 1994. Molecular determinants of the V3 loop of human immunodeficiency virus type 1 glycoprotein gp120 responsible for controlling cell tropism. J Gen Virol. 75:3249–3253.
8. Chesebro, B., 1992. Macrophage-tropic human immunodeficiency virus isolates from different patients exhibit unusual V3 envelope sequence homogenity in comparison with T-cell-tropic isolates: definition of critical amino acids involved in cell tropism. J Virol. 66:6547–6554.
9. Cho, M. W., 1998. Identification of determinants on a dualtropic human immunodeficiency virus type 1 envelope glycoprotein that confer usage of CXCR4. J Virol. 72:2509–2515.
10. Cocchi, F., 1996. The V3 domain of the HIV-1 gp120 envelope glycoprotein is critical for chemokine-mediated blockade of infection. Nat Med. 2:1244–1247.
11. Cormier, E. G., 2000. Specific interaction of CCR5 amino-terminal domain peptides containing sulfotyrosines with HIV-1 envelope glycoprotein gp120. Proc. Natl. Acad. Sci. USA. 97:5762–5767.
12. Doranz, B. J., 1997. Two distinct CCR5 domains can mediate coreceptor usage by human immunodeficiency virus type 1. J Virol. 71:6305–6314.
13. Dragic, T., 1998. Amino-terminal substitutions in the CCR5 coreceptor impair gp120 binding and human immunodeficiency virus type 1 entry. J Virol. 72:279–285.
14. Dragic, T., 2000. A binding pocket for a small molecule inhibitor of HIV-1 entry within the transmembrane helices of CCR5. Proc Natl Acad Sci U S A. 97:5639–5644.
15. Farzan, M., 1998. A tyrosine-rich region in the N terminus of CCR5 is important for human immunodeficiency virus type 1 entry and mediates an association between gp120 and CCR5. J Virol. 72:1160–1164.
16. Farzan, M., 1999. Tyrosine sulfation of the amino terminus of CCR5 facilitates HIV-1 entry. Cell. 96:667–676.
17. Farzan, M., 2000. A tyrosine-sulfated peptide based on the N-terminus of CCR5 interacts with a CD4-enhanced epitope of the HIV-1 gp120 envelope glycoprotein and inhibits HIV-1 entry. J Biol Chem: in press.
18. Harrowe, G., 1995. Amino acid substitutions in the V3 loop are responsible for adaptation to growth in transformed T-cell lines of a primary human immunodeficiency virus type 1. Virology. 210:490–494.
19. Hung, C. S., 1999. Analysis of the critical domain in the V3 loop of human immunodeficiency virus type 1 gp 120 involved in CCR5 utilization. J Virol. 73:8216–8226.
20. Hwang, S. S., 1991. Identification of the envelope V3 loop as the primary determinant of cell tropism in HIV-1. Science. 253:71–74.
21. Ivanoff, L., 1991. Alteration of HIV-1 infectivity and neutralization by a single amino acid replacement in the V3 loop domain. Aids Res. Hum. Retroviruses. 7:595–603.
22. Kwong, P. D., 1998. Structure of an HIV gp120 envelope glycoprotein in complex with the CD4 receptor and a neutralizing human antibody. Nature. 393:648–659.

23. Kwong, P. D., 2000. Oligomeric modeling and electrostatic analysis of the gp120 envelope glycoprotein of human immunodeficiency virus. J Virol. 74:1961–1972.
24. Menzo, S., 1998. Rare mutations in a domain crucial for V3-loop structure prevail in replicating HIV from long-term non-progressors. Aids. 12:985–997.
25. Moore, J., 1994. Probing the structure of the surface glycoprotein gp120 of human immunodeficiency virus type 1 with a panel of monoclonal antibodies. J. Virol. 68:469–484.
26. Moore, J., 1996. Antibody cross-competition analysis of the human immunodeficiency virus type 1 exterior envelope glycoprotein. J. Virol. 70:1863–1872.
27. Moore, J. P., 1991. The role of the V3 domain of gp120 in HIV infection. AIDS. 5(suppl.2):S21-S33.
28. Moore, J. P., 1995. A human monoclonal antibody to a complex epitope in the V3 region of human immunodeficiency virus type 1 has broad reactivity within and outside clade B. J. Virol. 69:122–130.
29. Morris, J. F., 1994. Effect of a single amino acid substitution in the V3 domain of the human immunodeficiency virus type 1: generation of revertant viruses to overcome defects in infectivity in specific cell types. J Virol. 68:8380–8385.
30. Moser, B., 1993. Interleukin-8 antagonists generated by N-terminal modification. J Biol Chem. 268:7125–7128.
31. Myszka, D. G., 2000. Energetics of the HIV gp120-CD4 binding reaction. Proc Natl Acad Sci U S A. 97:9026–9031.
32. Olsen, W. C., 1999. Differential inhibition of human immunodeficiency virus type 1 fusion, gp120 binding, and CC-chemokine activity by monoclonal antibodies to CCR5. J. Virol. 73:4145–4155.
33. Page, K., 1992. Analysis of mutations in the V3 domain of gp160 that affect fusion and infectivity. J Virol. 66:524–533.
34. Picard, L., 1997. Multiple extracellular domains of CCR-5 contribute to human immunodeficiency virus type 1 entry and fusion. J Virol. 71:5003–5011.
35. Rabut, G. E., 1998. Alanine substitutions of polar and nonpolar residues in the amino-terminal domain of CCR5 differently impair entry of macrophage- and dualtropic isolates of human immunodeficiency virus type 1. J. Virol. 72:3464–3468.
36. Rizzuto, C., 2000. Fine definition of a conserved CCR5-binding region on the human immunodeficiency virus type 1 glycoprotein 120. AIDS Res Hum Retroviruses. 16:741–749.
37. Rizzuto, C. D., 1998. A conserved HIV gp120 glycoprotein structure involved in chemokine receptor binding Science. 280:1949–1953.
38. Rucker, J., 1996. Regions in beta-chemokine receptors CCR5 and CCR2b that determine HIV-1 cofactor specificity. Cell. 87:437–446.
39. Samson, M., 1997. The second extracellular loop of CCR5 is the major determinant of ligand specificity. J Biol Chem. 272:24934–24941.
40. Sanders, R. W., 2000. Variable-loop-deleted variants of the human immunodeficiency virus type 1 envelope glycoprotein can be stabilized by an intermolecular disulfide bond between the gp120 and gp41 subunits. J. Virol. 74:5091–5100.
41. Shioda, T., 1992. Small amino acid changes in the V3 hypervariable region of gp120 can affect the T-cell-line and macrophage tropism of human immunodeficiency virus type 1. Proc Natl Acad Sci U S A. 89:9434–9438.
42. Trkola, A., 1996. CD4-dependent, antibody sensitive interactions between HIV-1 and its coreceptor CCR5. Nature. 384:184–186.
43. Verrier, F., 1999. Role of HIV type 1 glycoprotein 120 V3 loop in determining coreceptor usage. AIDS Res Hum Retroviruses. 15:731–743.
44. Wang,. W. K., 1999. Hypervariable region 3 residues of HIV type 1 gp120 involved in CCR5 coreceptor utilization: therapeutic and prophylactic implications. Proc Natl Acad Sci U S A. 96:4558–4562.
45. Wells, T. N., 1996. Selectivity and antagonism of chemokine receptors. J Leukoc Biol. 59:53–60.
46. Wu, L., 1996. CD4-induced interaction of primary HIV-1 gp120 glycoproteins with the chemokine receptor CCR-5. Nature. 384:179–183.
47. Wyatt, R., 1998. The HIV-1 envelope glycoproteins: fusogens, antigens and immunogens. Science. 280:1884–1888.

What is claimed:

1. A method of inhibiting human immunodeficiency virus infection of a CD4+ cell which also carries a CCR5 receptor on its surface which comprises contacting the CD4+ cell with an amount of a binding-inhibiting compound effective to inhibit binding of human immunodeficiency virus to the CCR5 receptor so as to thereby inhibit human immunodeficiency virus infection of the CD4+ cell, said binding-inhibiting compound comprising the structure

θαYDINYYTSEβλ wherein T represents a threonine, S represents a serine, E represents a glutamic acid, each Y represents a tyrosine, D represents an aspartic acid, I represents an isoleucine, and N represents an asparagine;

wherein α represents from 0 to 9 amino acids, with the proviso that if there are more than 2 amino acids, they are joined by peptide bonds in consecutive order and have a sequence identical to the sequence set forth in SEQ ID NO:1 beginning with the I at position 9 and extending therefrom in the amino terminal direction;

wherein β represents from 0 to 13 amino acids, with the proviso that if there are more than 2 amino acids, they are joined by peptide bonds in consecutive order and have a sequence identical to the sequence set forth in SEQ ID NO:1 beginning with the P at position 19 and extending therefrom in the carboxy terminal direction;

wherein θ represents an amino group or an acetylated amino group;

wherein λ represents a carboxyl group or an amidated carboxyl group;

wherein all of α, Y, D, I, N, Y, Y, T, S, E and β are joined together by peptide bonds;

further provided that at least two of the tyrosines represented by Y in the YDINYYTSE portion of the structure of the compound are sulfated.

2. A method of identifying an agent which inhibits binding of a CCR5 ligand to a CCR5 receptor which comprises:
  (a) immobilizing the binding-inhibiting compound of claim 1 on a solid support;
  (b) contacting the immobilized compound from step (a) with sufficient detectable CCR5 ligand to saturate all binding sites for the CCR5 ligand on the immobilized compound under conditions permitting binding of the CCR5 ligand to the immobilized compound so as to form a complex;
  (c) removing any unbound CCR5 ligand;
  (d) contacting the complex from step (b) with the agent; and
  (e) detecting whether any CCR5 ligand is displaced from the complex, wherein displacement of detectable CCR5 ligand from the complex indicates that the agent binds to the compound so as to thereby identify the agent as one which inhibits binding of the CCR5 ligand to the CCR5 receptor.

3. A method of identifying an agent which inhibits binding of a CCR5 ligand to a CCR5 receptor which comprises:
  (a) contacting the compound of claim 1 with the agent and detectable CCR5 ligand under conditions permitting binding of the CCR5 ligand to the compound so as to form a complex;
  (b) removing any unbound CCR5 ligand;
  (c) measuring the amount of detectable CCR5 ligand which is bound to the compound in the complex;
  (d) measuring the amount of detectable CCR5 ligand which binds to the compound in the absence of the agent; and
  (e) comparing the amount of CCR5 ligand which is bound to the compound in step (c) with the amount measured in step (d), wherein a reduced amount measured in step (c) indicates that the agent binds to the compound or CCR5 ligand so as to thereby identify the agent as one which inhibits binding of the CCR5 ligand to the CCR5 receptor.

4. A method of identifying an agent which inhibits binding of a CCR5 ligand to a CCR5 receptor which comprises:
  (a) immobilizing the binding-inhibiting compound of claim 1 on a solid support;
  (b) contacting the immobilized compound from step (a) with the agent dissolved or suspended in a known vehicle and measuring the binding signal generated by such contact;
  (c) contacting the immobilized compound from step (a) with the known vehicle in the absence of the compound and measuring the binding signal generated by such contact; and
  (d) comparing the binding signal measured in step (b) with the binding signal measured in step (c), wherein an increased amount measured in step (b) indicates that the agent binds to the compound so as to thereby identify the agent as one which binds to the CCR5 receptor.

5. A method of obtaining a composition which comprises:
(a) identifying a compound which inhibits binding of a CCR5 ligand to a CCR5 receptor according to the method of claim 2: and
(b) admixing the compound so identified or a homolog or derivative thereof with a carrier.

6. A compound having the structure:

wherein each T represents a threonine, each S represents a serine, each E represents a glutamic acid, each Y represents a tyrosine; each D represents an aspartic acid, I represents an isoleucine and N represents an asparagine;

wherein α represents from 0 to 9 amino acids, with the proviso that if there are more than 2 amino acids, they are joined together by peptide bonds in consecutive order and have a sequence identical to the sequence set forth in SEQ ID NO:1 beginning with the I at position 9 and extending therefrom in the amino terminal direction;

wherein β represents from 0 to 13 amino acids, with the proviso that if there are more than 2 amino acids, they are joined together by peptide bonds in consecutive order and have a sequence identical to the sequence set forth in SEQ ID NO:1 beginning with the P at position 19 and extending therefrom in the carboxy terminal direction;

wherein λ represents a carboxyl group or an amidated carboxyl group;

wherein all of α, Y, D, I, N, Y, Y, T, S, E and β are joined together by peptide bonds, further provided that at least two tyrosines represented by Y in the YDINYYTSE structure of the compound are sulfated, and wherein Π is an integer from 1 to 8, Δ is a polymer, and the solid line represents up to 8 linkers which attach the structure in parentheses to Δ.

7. A composition comprising the binding-inhibiting compound of claim 1 and a detectable marker attached thereto.

8. A composition which comprises a carrier and an amount of the binding-inhibiting compound of claim 1 effective to inhibit binding of HIV-1 to a CCR5 receptor on the surface of a CD4+ cell.

9. A method of identifying an agent which inhibits binding of a CCR5 ligand to a CCR5 receptor which comprises:
(a) contacting the binding-inhibiting compound of claim 1 with sufficient detectable CCR5 ligand to saturate all binding sites for the CCR5 ligand on the compound under conditions permitting binding of the CCR5 ligand to the compound so as to form a complex;
(b) removing any unbound CCR5 ligand;
(c) measuring the amount of CCR5 ligand which is bound to the compound in the complex;
(d) contacting the complex from step (a) with the agent so as to displace CCR5 ligand from the complex;
(e) measuring the amount of CCR5 ligand which is bound to the compound in the presence of the agent; and
(f) comparing the amount of CCR5 ligand bound to the compound in step (e) with the amount measured in step (c), wherein a reduced amount measured in step (e) indicates that the agent binds to the compound so as to thereby identify the agent as one which inhibits binding of the CCR5 ligand to the CCR5 receptor.

10. A method of identifying an agent which inhibits binding of a CCR5 ligand to a CCR5 receptor which comprises:
(a) immobilizing the binding-inhibiting compound of claim 1 on a solid support;
(b) contacting the immobilized compound from step (a) with the agent and detectable CCR5 ligand under conditions permitting binding of the CCR5 ligand to the immobilized compound so as to form a complex;
(c) removing any unbound CCR5 ligand;
(d) measuring the amount of detectable CCR5 ligand which is bound to the immobilized compound in the complex;
(e) measuring the amount of detectable CCR5 ligand which binds to the immobilized compound in the absence of the agent;
(f) comparing the amount of CCR5 ligand which is bound to the immobilized compound in step (e) with the amount measured in step (d), wherein a reduced amount measured in step (d) indicates that the agent binds to the compound or CCR5 ligand so as to thereby identify the agent as one which inhibits binding of the CCR5 ligand to the CCR5 receptor.

11. A compound having the structure:

wherein T represents a threonine, S represents a serine, E represents a glutamic acid, each Y represents a tyrosine, D represents an aspartic acid, I represents an isoleucine, and N represents an asparagine;

wherein α represents from 0 to 9 amino acids, with the proviso that if there are more than 2 amino acids, they are joined together by peptide bonds in consecutive order and have a sequence identical to the sequence set forth in SEQ ID NO:1 beginning with the I at position 9 and extending therefrom in the amino terminal direction;

wherein β represents from 0 to 13 amino acids, with the proviso that if there are more than 2 amino acids, they are joined together by peptide bonds in consecutive order and have a sequence identical to the sequence set forth in SEQ ID NO:1 beginning with the P at position 19 and extending therefrom in the carboxy terminal direction;

wherein θ represents an amino group or an acetylated amino group;

wherein all of α, Y, D, I, N, Y, Y, T, S, E and β are joined together by peptide bonds, further provided that at least two of the tyrosines represented by Y in the YDINYYTSE structure of the compound are sulfated, and wherein Π is an integer from 1 to 8, Δ is a polymer, and the solid line represents up to 8 linkers which attach the structure in parentheses to Δ.

12. A compound comprising the structure:

wherein E represents a glutamic acid, and each Y represents a tyrosine;

wherein α represents from 0 to 9 amino acids, with the proviso that if there are more than two amino acids, they are joined by peptide bonds in consecutive order and have a sequence identical to the sequence set forth in SEQ ID NO:1 beginning with the I at position 9 and extending therefrom in the amino terminal direction;

wherein β represents from 0 to 13 amino acids, with the proviso that if there are more than 2 amino acids, they are joined by peptide bonds in consecutive order and have a sequence identical to the sequence set forth in SEQ ID NO:1 beginning with the P at position 19 and extending therefrom in the carboxy terminal direction;

wherein θ represents an amino group or an acetylated amino group;

wherein λ represents a carboxyl group or an amidated carboxyl group;

wherein Π represents any amino acid;

wherein all of α, Y, D, Π, Π, Y, Π, Π, Π, E and β are joined together by peptide bonds; and further provided that the two tyrosines represented by Y in the YDΠΠΠYΠΠΠΠE structure of the compound are sulfated.

* * * * *